United States Patent [19]
Piwinski et al.

[11] Patent Number: 5,104,876
[45] Date of Patent: Apr. 14, 1992

[54] BENZOPYRIDO PIPERIDINE, PIPERIDYLIDENE AND PIPERAZINE COMPOUNDS, COMPOSITIONS, METHODS OF MANUFACTURE AND METHODS OF USE

[75] Inventors: John J. Piwinski, Parsippany; Jesse K. Wong, Union; Michael J. Green, Skillman; Ashit K. Ganguly, Upper Montclair; Frank J. Villani, Fairfield, all of N.J.

[73] Assignee: Schering Corporation

[21] Appl. No.: 598,667

[22] PCT Filed: Apr. 26, 1989

[86] PCT No.: PCT/US89/01688

§ 371 Date: Oct. 26, 1990

§ 102(e) Date: Oct. 26, 1990

Related U.S. Application Data

[63] Continuation-in-part of Ser. No. 187,604, Apr. 28, 1988, abandoned.

[51] Int. Cl.$^5$ .................. A61K 31/495; A61K 31/44; A61K 31/445; C07D 487/00
[52] U.S. Cl. .................. 514/254; 514/253; 514/284; 514/285; 514/290; 514/291; 544/257; 544/296; 544/361; 546/15; 546/80; 546/89; 546/93; 546/101; 546/286; 546/323
[58] Field of Search .......... 544/361, 230, 296, 357, 544/361; 546/80, 89, 93, 15, 101, 323, 286; 514/290, 291, 254, 826, 253, 284, 285

[56] References Cited

U.S. PATENT DOCUMENTS

| | | | |
|---|---|---|---|
| 3,325,501 | 6/1967 | Ettingen et al. | 514/849 |
| 3,803,154 | 4/1974 | Drukker | 514/960 |
| 3,966,944 | 6/1976 | Carter | 514/318 |
| 4,609,664 | 9/1986 | Hasspacher | 546/196 |

*Primary Examiner*—Cecilia Shen

[57] ABSTRACT

Novel benzopyrido piperidiene, piperidylidene and piperazine compounds of the generalized formula

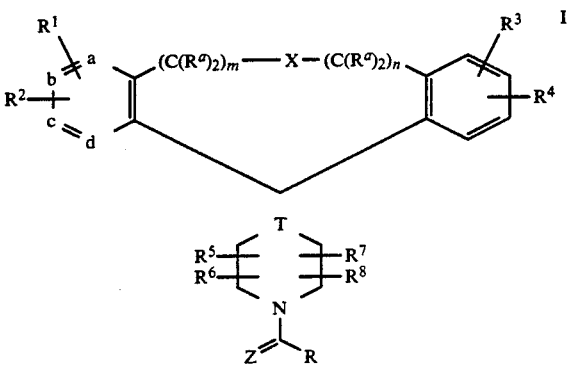

are disclosed as useful for the treatment of asthma, allergy and inflammation. Novel pharmaceutical compositions containing such compounds and processes for producing the compounds are also disclosed.

13 Claims, No Drawings

BENZOPYRIDO PIPERIDINE, PIPERIDYLIDENE AND PIPERAZINE COMPOUNDS, COMPOSITIONS, METHODS OF MANUFACTURE AND METHODS OF USE

The present application is the United States national application corresponding to International Application No. PCT/US89/01688 filed Apr. 26, 1989 and designating the United States, which PCT application is in turn a continuation-in-part of U.S. application Ser. No. 187,604 filed Apr. 28, 1988, which is now abandoned, the benefit of which applications is claimed pursuant to the provisions of 35 U.S.C. §§120,363 and 365(c).

BACKGROUND OF THE INVENTION

The present invention relates to certain benzopyrido piperidine, piperazine and piperidylidene compounds, compositions and methods of use.

The following references have disclosed oxygen or sulfur in the bridgehead of the three ring portion of the molecule:

Canadian Application 780,443, published in the name of Sandoz Patents Ltd.;

Eire 17764, published Apr. 5, 1964 in the name of Sandoz Patents Ltd.;

European Patent Application 81816337.6, Sandoz A.G., published Mar. 10, 1982;

Belgian Application 638,971, Sandoz S.A., published Apr. 21, 1964;

Belgian Application 644,121, Sandoz S.A., published Aug. 20, 1964;

U.S. Pat. No. 4,609,664, issued to Hasspacher on Sept. 2, 1986;

U.S. Pat. No. 3,966,944, issued to Carter on June 29, 1976;

U.S. Pat. No. 3,803,153, issued to Villani on Apr. 9, 1974;

U.S. Pat. No. 3,803,154, issued to Drukker on Apr. 9, 1974;

U.S. Pat. No. 3,325,501, issued to Ettinsen et al. on June 13, 1967;

None of the references disclose substitution on the piperidylidene, piperidine or piperazine nitrogen similar to that set forth below.

SUMMARY OF THE INVENTION

Compounds represented by the structural formula I

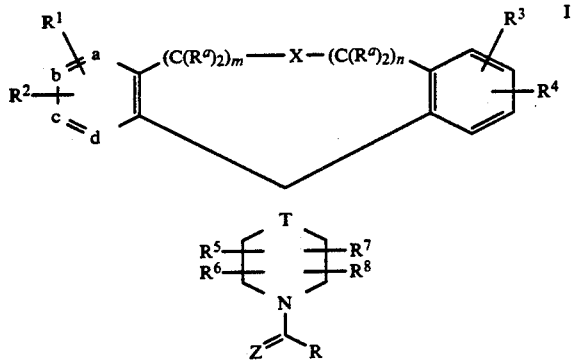

or a pharmaceutically acceptable salt or solvate thereof, wherein:

one of a, b, c and d represents nitrogen or $-NR^{11}-$, where $R^{11}$ is $-O^-$, $-CH_3$ or $-(CH_2)_pCO_2H$ where p is 1 to 3, and the remaining a, b, c and d groups are CH which may be substituted with $R^1$ or $R^2$;

$R^1$ and $R^2$ may be the same or different and each independently represents halo, $-CF_3$, $-OR^{10}$, $-C(O)R^{10}$, $-S(O)_eR^{12}$ where e is 0, 1 or 2, $-N(R^{10})_2$, $-NO_2$, SH, CN, $-OC(O)R^{10}$, $-CO_2R^{10}$, $-OCO_2R^{12}$, $-NR^{10}C(O)R^{10}$, alkyl, alkenyl or alkynyl, which alkyl or alkenyl groups may be substituted with halo, $-OR^{10}$ or $-CO_2R^{10}$, or $R^1$ and $R^2$ may together form a benzene ring fused to the pyridine ring;

$R^{10}$ represents H, alkyl or aryl;

$R^{12}$ represents alkyl or aryl;

$R^3$ and $R^4$ may be the same or different and each independently represents H or any of the substituents of $R^1$ and $R^2$, or $R^3$ and $R^4$ may be taken together to represent a saturated or unsaturated $C_5$-$C_7$ ring fused to the benzene ring;

$R^5$, $R^6$, $R^7$ and $R^8$ each independently represents H, $-CF_3$, $-CO_2R^{10}$, $-C(O)R^{10}$, alkyl or aryl, which alkyl or aryl may be substituted with $-OR^{10}$, $-SR^{10}$, $-N(R^{10})_2$, $-NO_2$, $-C(O)R^{10}$, $-OC(O)R^{12}$, $-OCO_2R^{12}$, $-CO_2R^{10}$ and $-OPO_3(R^{10})_2$, or one of $R^5$, $R^6$, $R^7$ and $R^8$ may be taken in combination with R as defined below to represent $-(CH_2)_r-$ where r is 1 to 4, said combination being optionally substituted with lower alkyl, lower alkoxy, $-CF_3$ or aryl, or $R^5$ may be combined with $R^6$ to represent $=O$ or $=S$, and/or $R^7$ may be combined with $R^8$ to represent $=O$ or $=S$;

T represents carbon or nitrogen, with the dotted line attached to T representing an optional double bond when T is carbon;

m and n are integers 0, 1, 2, or 3, such that the sum of m plus n equals 0 to 3;

when m plus n equals 1, X represents $-O-$, $-S(O)_e-$ where e is 0, 1 or 2, $-NR^{10}-$, $-C(O)NR^{10}-$, $-NR^{10}C(O)-$, $-C(S)NR^{10}-$, $-NR^{10}C(S)-$, $-CO_2-$ or $-O_2C-$, where $R^{10}$ is as defined above;

when m plus n equals 2, X represents $-O-$, $-S(O)_e-$ where e is 0, 1 or 2, or $-NR^{10}$;

when m plus n represents 0, X can be any substituent for m plus n equalling 1 and X can also be a direct bond, cyclopropylene or propenylene;

when m plus n equals 3 then X equals a direct bond;

each $R^a$ may be the same or different, and each independently represents H, lower alkyl or phenyl;

Z represents $=O$, $=S$ or $=NR^{13}$ with $R^{13}$ equal to $R^{10}$ or $-CN$, wherein $R^{10}$ is as defined above, such that (a) when Z is O, R may be taken in combination with $R^5$, $R^6$, $R^7$ or $R^8$ as defined above, or R represents H, alkyl, aryl, $-SR^{12}$, $-N(R^{10})_2$, cycloalkyl, alkenyl, alkynyl or $-D$ wherein $-D$ represents heterocycloalkyl,

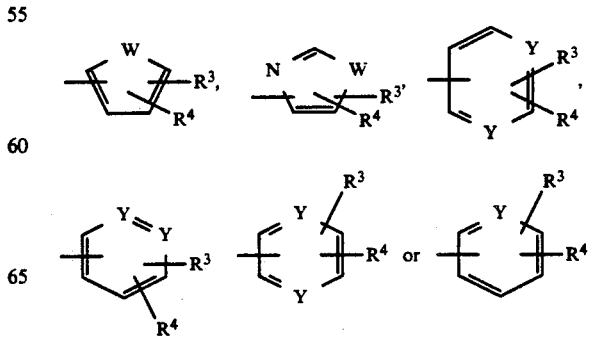

wherein $R^3$ and $R^4$ are as previously defined and W is O, S or $NR^{10}$, and where Y is N or $NR^{11}$, said cycloalkyl, alkyl, alkenyl and alkynyl being optionally substituted with from 1-3 groups selected from halo, $-CON(R^{10})_2$, aryl, $-CO_2R^{10}$, $-OR^{14}$, $-SR^{14}$, $-N(R^{10})_2$, $-N(R^{10})CO_2R^{10}$, $-COR^{14}$, $-NO_2$ or $-D$, wherein $-D$ and $R^{10}$ are as defined above and $R^{14}$ represents $R^{10}$, $-(CH_2)_rOR^{10}$ or $-(CH_2)_qCO_2R^{10}$ wherein r is 1 to 4, q is 0 to 4;

said alkenyl and alkynyl R groups not containing $-OH$, $-SH$ or $-N(R^{10})_2$ on a carbon in a double or triple bond respectively; and (b) when Z represents $=S$, R represents in addition to those R groups above, aryloxy or alkoxy; and (c) where Z represents $=NR^{13}$, R represents H, alkyl, aryl, $N(R^{10})_2$, cycloalkyl, alkenyl or alkynyl.

In a preferred embodiment of the invention, d represents nitrogen or $NR^{11}$, and the a, b, and c groups are CH, which may be substituted with $R^1$ or $R^2$.

Preferred values of $R^1$ are halo, alkyl and $-OR^{10}$ and $-N(R^{10})_2$ where $R^{10}$ is preferably H or alkyl.

Preferred values of $R^2$ are identical to those preferred $R^1$ groups, and most preferably neither $R^1$ nor $R^2$, or only one of $R^1$ and $R^2$ is present.

Preferred values of $R^3$ and $R^4$ are halo, alkyl, $-CF_3$ or $-OR^{10}$, with preferred $R^{10}$ values equal to H or alkyl. More preferably only of $R^3$ and $R^4$ is present, and represents halo or alkyl, most preferably halo, and in particular, chloro or bromo.

Preferred values of $R^5$, $R^6$, $R^7$ and $R^8$ are H, alkyl or $-CO_2R^{10}$ where $R^{10}$ is H or alkyl. More preferably at most one of $R^5$, $R^6$, $R^7$ and $R^8$ is alkyl, the remaining groups being H. Most preferably all four $R^5$, $R^6$, $R^7$ and $R^8$ are H.

Preferred values of $R^{10}$ are H or alkyl, and most preferably H.

The preferred value of $R^{11}$ is $-O^{31}$.

Preferred values of X when m plus n is zero are a direct bond, $-O-$, and $-S(O)_e-$, where e is 0, 1 or 2, and most preferably e is zero.

Preferred substituents for X when m plus n is 1 or 2 are $-O-$ and $-S(O)_e-$ with e equal to zero.

The preferred substituent for Z is $=O$.

Preferred substituents for R are H and alkyl, most preferably alkyl and in particular, lower alkyl.

The preferred substituents for T are carbon with a double bond present or nitrogen.

Preferred species falling within the scope of the invention include:

1-acetyl-4-(10H-[1]benzothiopyrano[3,2-b]pyridin-10-ylidene)piperidine;

1-acetyl-4-(8-chloro-5,11-dihydro[1]benzoxepino [4,3-b]pyridin-11-ylidene)piperidine;

1-acetyl-4-(10H-[1]-benzoypyrano[3,2-b]pyridine-10-ylidene)piperidene;

4-(10H-[1]-benzopyrano[3,2-b]pyridin-10-ylidene)-1-piperidine carboxaldehyde;

1-acetyl-4-(5H-benzoypyrano[2,3-b]pyridin-5-ylidene)-piperidine;

1-acetyl-4-(5,6,7,12-tetrahydrobenzo[6,7]cycloocta[1,2-b]pyridin-12-ylidene)piperidine;

11-(1-acetyl-4-piperidinylidene)-8-chloro-5,11-dihydro-[1]-benzothiepino[4,3-b]pyridine;

11-(1-acetyl-4-piperidinylidene)-8-chloro-5,11-dihydro-[1]-benzothiepino[4,3-b]pyridine 1,6-dioxide;

11-(1-acetyl-4-piperidinylidene)-8-chloro-5,11-dihydro-[1]-benzothiepino[4,3-b]pyridine 6,6-dioxide;

11-(1-acetyl-4-piperidinylidene)-8-chloro-5,11-dihydro-[1]-benzothiepino[4,3-b]pyridine-6-oxide;

11-(1-acetyl-4-piperidinylidene)-8-chloro-5,11-dihydro-[1]-benzothiepino[4,3-b]pyridine -1,6,6-trioxide;

1-acetyl-4-(9H-indeno[2,1-b]pyridin-9yl)-piperazine; and 1-(4-pyridinylcarbonyl)-4-(5,6,7,12-tetrahydrobenzocyclooocta[1,2-b]pyridin-12-ylidene)-piperidine N'-oxide The invention described herein also encompasses a pharmaceutical composition comprising a compound represented by structural formula I in combination with a pharmaceutically acceptable carrier.

The invention further encompasses a method of treating asthma, allergy and/or inflammation in a mammal in need of such treatment, comprising administering a compound of formula I to said mammal in an amount effective to treat allergy, asthma and/or inflammation, respectively.

The present invention also is directed at the use of a compound of formula I and its pharmaceutically acceptable salts for the preparation of a medicament for the treatment of asthma, allergy and/or inflammation.

The present invention also comprises a method of preparing a pharmaceutical composition comprising admixing a compound of formula I with a pharmaceutically acceptable carrier.

This invention also is directed at a method of manufacturing a compound of formula I comprising:

(A) reacting a compound of formula II with a compound of formula III

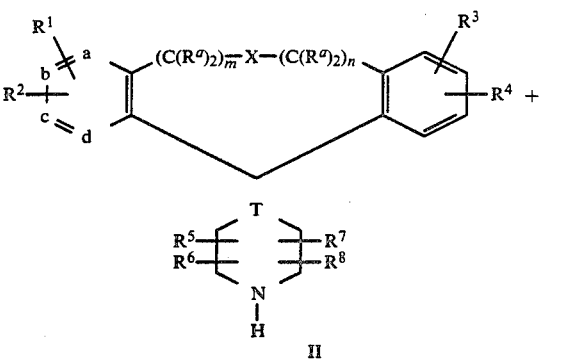

where L represents a suitable leaving group; and (B) reacting a compound of formula V with a suitable compound of formula III

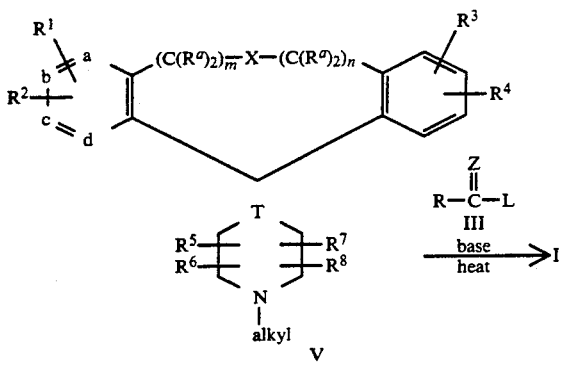

(C) Cyclizing a compound of formula XLV to a compound of the formula I.

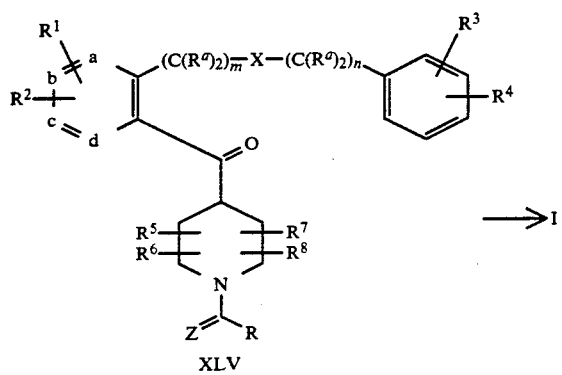

(D) Reacting a compound of formula XXX with a compound of formula XXXII or XXIX to produce a compound of formula I if $R^c$ is Z(C)R.

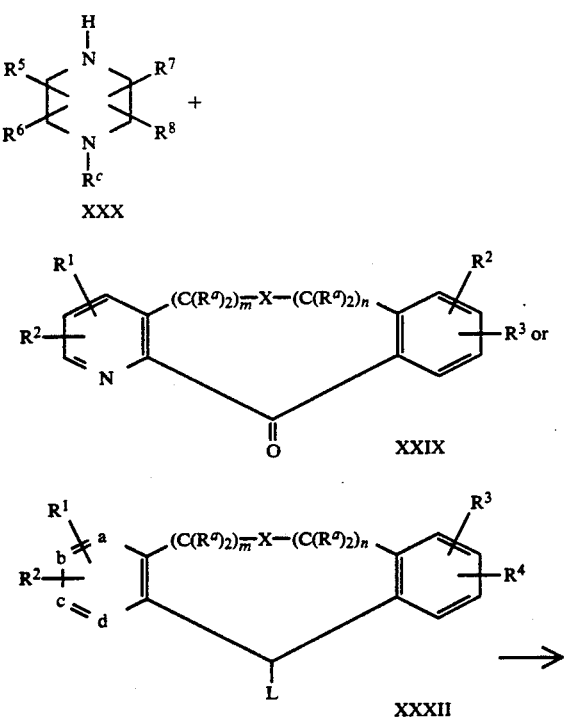

DETAILED DESCRIPTION

As used herein, the following terms are used as defined below unless otherwise indicated:

alkyl - (including the alkyl portions of alkoxy, alkylamino and dialkylamino) - represents straight and branched carbon chains and having from one to twenty carbon atoms;

lower alkyl - subset of alkyl as defined above, having from one to six carbon atoms;

alkanediyl - represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, $-CH_2CH_2CH_2-$, $-CH_1CHCH_3$, $-CH_1CH_2CH_3$, etc.

cycloalkyl - represents saturated carbocyclic rings branched or unbranched of from 3 to 20 carbon atoms, preferably 3 to 7 carbon atoms;

heterocycloalkyl - represents a saturated, branched or unbranched carbocyclic ring having from 3 to 15 carbon atoms, preferably from 4 to 6 carbon atoms, which carbocyclic ring is interrupted by 1 to 3 hetero groups selected from $-O-$, $-S-$ or $-NR^{10}-$(suitable heterocycloalkyl groups including 2- or 3-tetrahydrofuranyl, 2- or 3-tetrahydrothienyl, 2- , 3-or 4-piperidinyl, 2- or 3-pyrrolidinyl, 2- or 3-piperizinyl, 2- or 4-dioxanyl, etc.);

alkenyl - represents straight and branched carbon chains having at least one carbon to carbon double bond and having from 2 to 12 carbon atoms, preferably from 3 to 6 carbon atoms;

alkynyl - represents straight and branched carbon chains having at least one carbon to carbon triple bond and having from 2 to 12 carbon atoms, preferably from 2 to 6 carbon atoms;

aryl (including the aryl portion of aryloxy)—represents a carbocyclic group having from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, $-COOR^{10}$ or $-NO_2$; and halo - represents fluoro, chloro, bromo and iodo.

Certain compounds of the invention may exist in different isomeric as well as conformational forms. The invention contemplates all such isomers and conformers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the pyridine and benzene rings of formula I may contain one or more substituents $R^1$, $R^2$, $R^3$ and $R^4$. Similarly, the heterocyclic ring D may contain one or more of $R^3$ and $R^4$. In compounds where there is more than one such substituent, they may be the same or different. Thus compounds having combinations of such substituents are within the scope of the invention. Also, the lines drawn into the rings from the $R^1$ through $R^8$ groups indicate that such groups may be attached at any of the available positions. For example, the $R^1$ and $R^2$ groups may be attached at the 1, 2, 3 or 4 positions while the $R^3$ and $R^4$ groups may be attached at any of the available positions.

Numbering the compounds of the invention varies with the size of the center ring. However, numbering the piperidine, piperidylidene or piperazine remains consistent, with the nitrogen at the bottom designated 1', the carbon atom to the left designated 2', and the numbers increasing in a clockwise fashion. Hence, the carbons to the left and right of the nitrogen at the bottom are 2' and 6' respectively.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amine, hydroxyalkylamines, N-methylglucamine and the like.

Certain basic compounds of the invention also form pharmaceutically acceptable salts, e.g., acid addition salts. For example, the pyrido- or pyrazino-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methane-sulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

All such acid and base salts (e.g. pyridinyl nitrogen salts) are intended to be pharmaceutically acceptable salts within the scope of the invention and all acid and base salts are considered equivalent to the free forms of the corresponding compounds for purposes of the invention.

The following processes may be employed to produce compounds of general structural formula I.

A. A compound of general formula II may be reacted with compound III with and sometimes without the presence of base to produce compounds of general structural formula I.

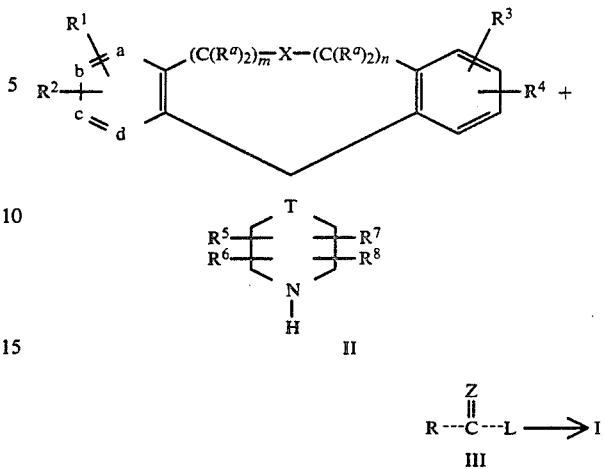

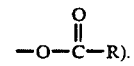

Representative examples of appropriate bases are pyridine and triethylene. L designates a suitable leaving group. For example, if Z is O or S, a compound of compound III may be an acyl halide (e.g., L=halo) or acyl anhydride, (e.g., L is $$-O-\overset{\overset{O}{\|}}{C}-R).$$

Alternatively, if the leaving group is hydroxy a coupling reagent may be employed to form Compound I. Examples of coupling agents include N,N'-dicyclohexylcarbodiimide (DCC), 1-(3-dimethylaminopropyl-3-ethylcarbodiimide (DEC) and N,N'-carbonyldiimidazole (CDI). The leaving group may also be alkoxy, in which case the compounds of formula I may be produced by refluxing a compound of formula II with an excess of a compound of formula III.

If $Z=NR^{13}$, the compounds of the invention are prepared by substituting into the preparative reaction for compound III an appropriately substituted imino chloride or imino ether (e.g., Z=NH, L=Cl or $OCH_2CH_3$).

Compounds of general formula II may be prepared by cleaving the group $COOR^b$ from the corresponding carbamates IV, for example, via acid hydrolysis (e.g., HCl) or base hydrolysis (e.g., KOH):

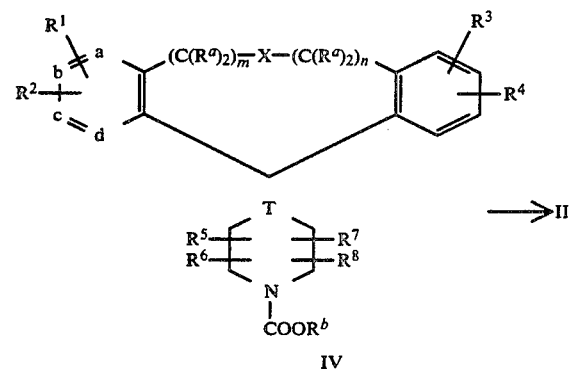

wherein $R^b$ is a group which does not prevent the cleavage reaction, e.g., $R^b$ is an optionally substituted alkyl such as ethyl, or 2,2,2-trichloroethyl.

Alternatively, depending upon the nature of $R^b$, as determined by one skilled in the art, Compound IV may be treated with an organometallic reagent (e.g., CH$_3$Li), a reductive reagent (e.g., Zn in acid), etc., to form compounds of formula II.

Compound IV may be prepared from the N-alkyl compound shown as formula V below, in the manner disclosed in U.S. Pat. Nos. 4,282,233 and 4,335,036.

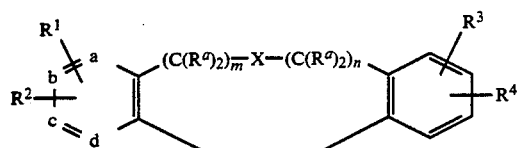
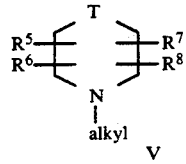

V

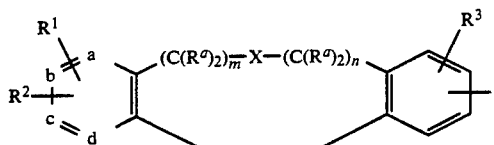
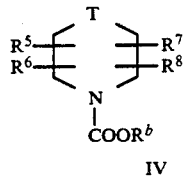

COOR$^b$

IV

There are numerous other methods for converting Compound V to Compound II. For example, treatment of Compound V with BrCN via von braun reaction conditions would provide nitrile VI as shown below. Subsequent hydrolysis of the nitrile under either aqueous basic or acidic conditions would produce Compound II. This method is preferable when there is substitution on the piperidine ring.

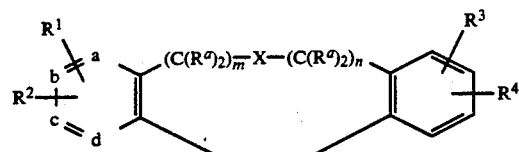
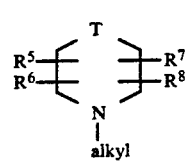

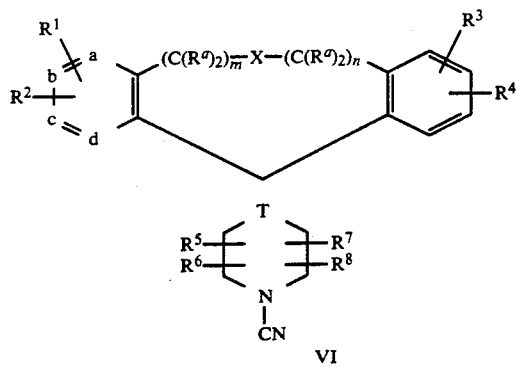
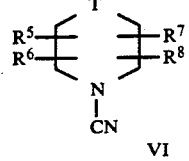

CN

VI

B. The compounds of formula I where Z is O or S may be made by an alternative process using direct conversion of the N-alkyl compound V with an appropriate compound of formula III such as an acyl halide or acyl anhydride. Preferably the reaction is run in the presence of an appropriate nucleophile (e.g. LiI, etc.) and solvent (e.g., toluene, dioxane or xylenes). An appropriate base, may be added, and heating may be required. Typically, a temperature ranging from 50°–150° C. (preferably 100°–120° C.) is utilized.

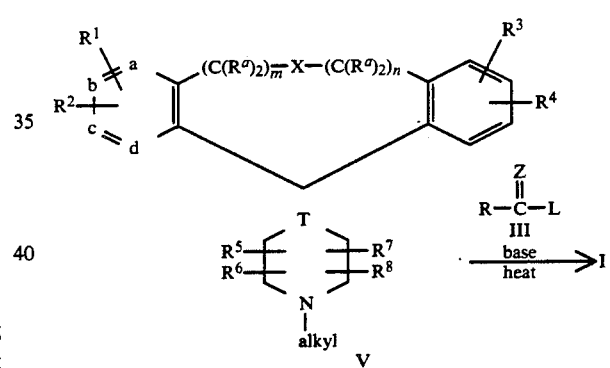
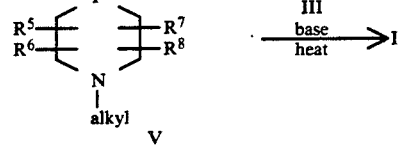

V

Compound V is prepared as described in part A above.

When m and n are each zero and X is not a direct bond, the compounds of formula V may be prepared using the teachings of U.S. Pat. Nos. 3,803,153; 3,803,154 and 3,325,501. Hence, a ketone of compound VII is reacted with a piperidyl grignard reagent VIII or similar metalated reagent to form the piperidyl compound IX, which is dehydrated to form compound X. Compound X may be converted to a compound of the invention as previously described.

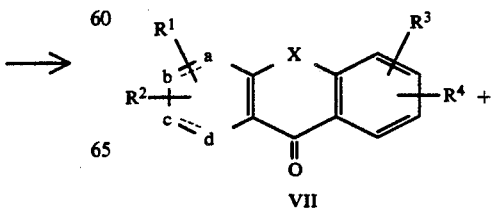

VII

-continued

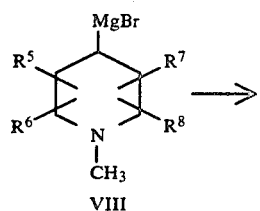

VIII

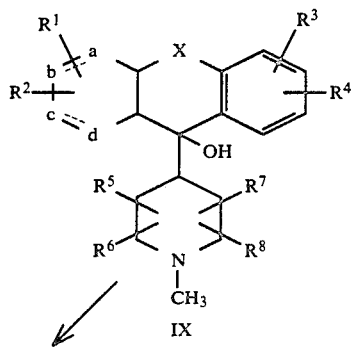

IX

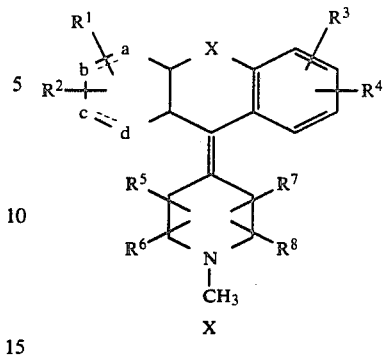

When m and n are each zero, and X represents a direct bond, the reaction scheme below may be utilized. For purposes of illustration, in the reaction scheme below, d has been designated as representing =N—. However, a, b or c could similarly represented =N—.

The N-oxide of compound XI may be alkylated (e.g. dimethyl sulfate) in order to generate a leaving group and then treated with cyanide anion to form the cyanate compound XIII. The cyano derivative XIII can then be cyclized to the cyclic ketone XIV using $CF_3SO_3H$ or a similar reagent. The reaction is substrate dependent and should be monitored by TLC and usually requires elevated temp. (e.g. 100° C.). The ketone XIV is then usually reacted with the grignard reagent or other metalated reagent of the appropriately substituted —N—alkyl piperidine to form the carbinol XVI. The reaction is usually carried out in an inert solvent such as THF and between −78° C. to +60° C. Other alternatives are possible such as the reductive coupling of the halo piperidine with the ketone using Na in $NH_3$. Dehydration of carbinol XVI to XVII can be accomplished using a variety of conditions. Acidic conditions such as $CF_3SO_3H$, PPA or HCl in acetic acid are usually preferred. Compound XVII is then converted to compounds of the invention as previously described.

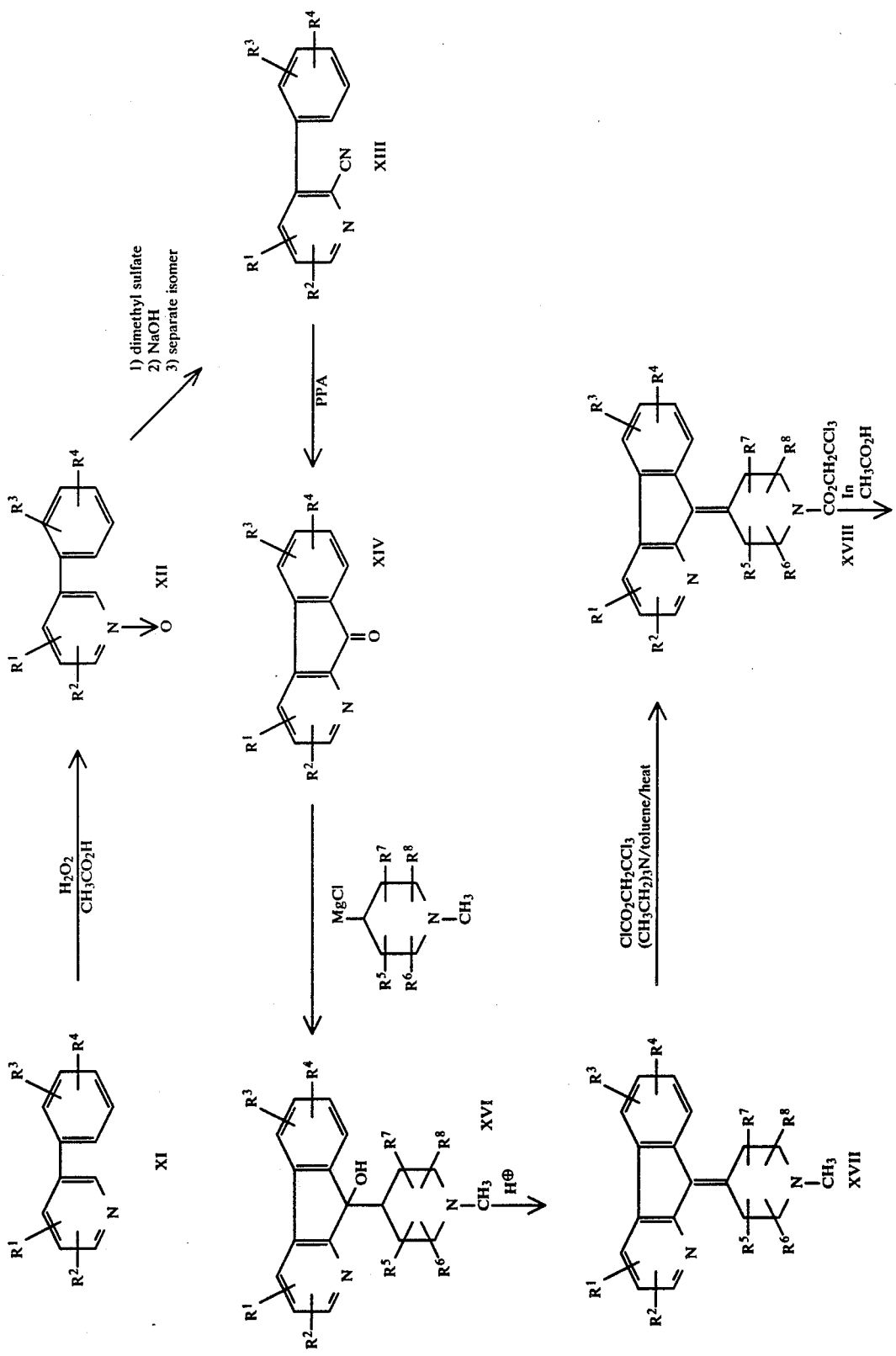

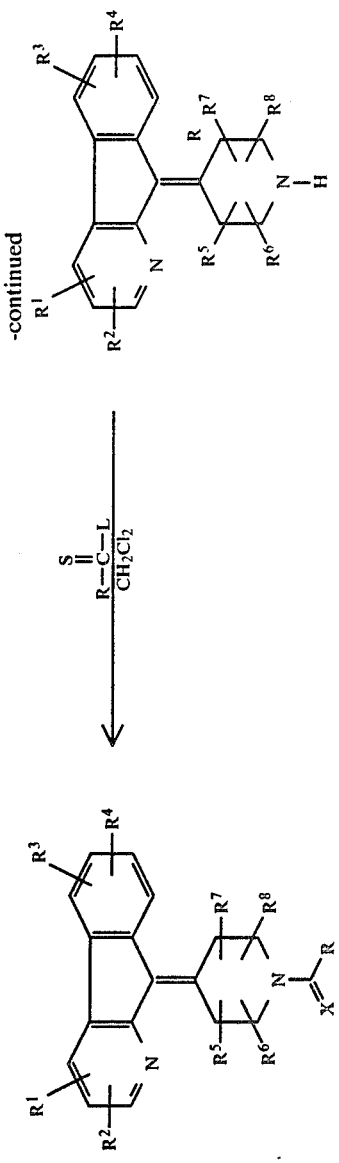

For compounds of formula I where m plus n is 3 and X is a direct bond, the following general reaction scheme may be used. As described above, for purposes of illustration, d has been designated =N—, and a, b and c are =CH— or substituted with R¹ or R². However, a, b and c could be used to designate =N— therein.

with the appropriate nucleophile. This displacement is normally conducted in the presence of base and an inert solvent, such as THF or toluene at elevated temperature. In this way, the haloalkyl-cyanopyridine derivative XXVII may be coupled to an appropriate alcohol, thiol or other appropriately substituted benzene derivative. The leaving group and nucleophile can be inter-

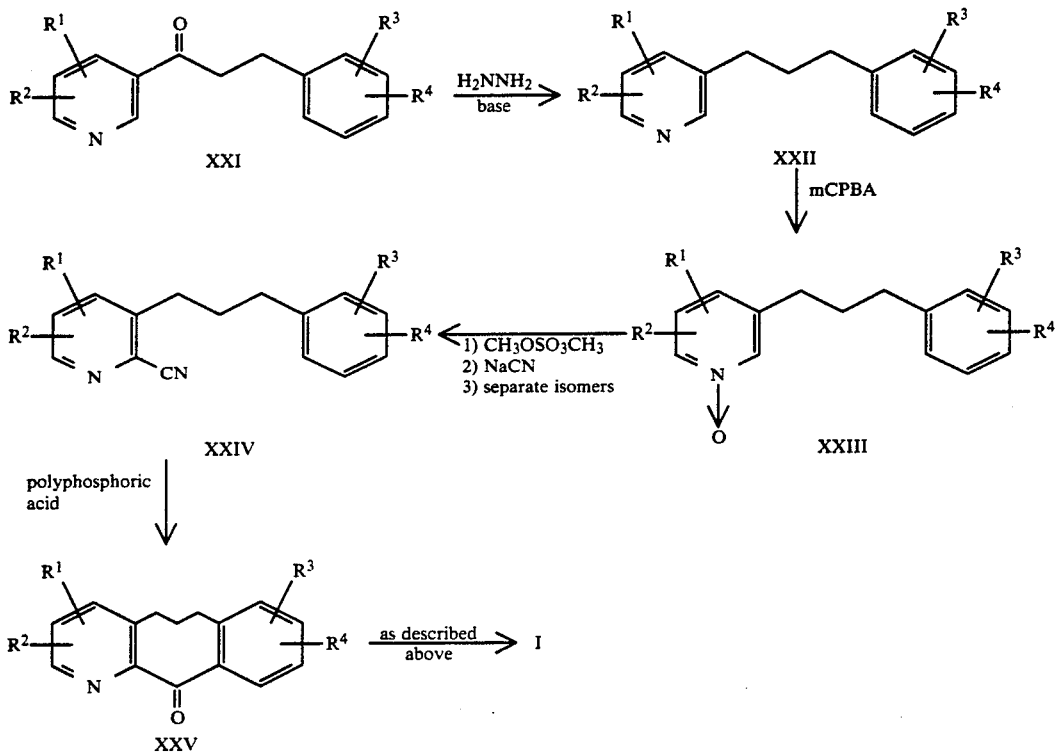

Compound XXV is then converted to I as previously described.

For compounds where X in the bridgehead is other than a direct bond and the sum of m plus n is 1, 2 or 3, the compounds may generally be prepared by reaction of the appropriate alkyl halide or similar electrophile changed such that the pyridine derivative contains the nucleophile X', and the substituted benzene derivative contains a leaving group L. Compound XXVIII can be converted to compound XXIX via the previously described procedure.

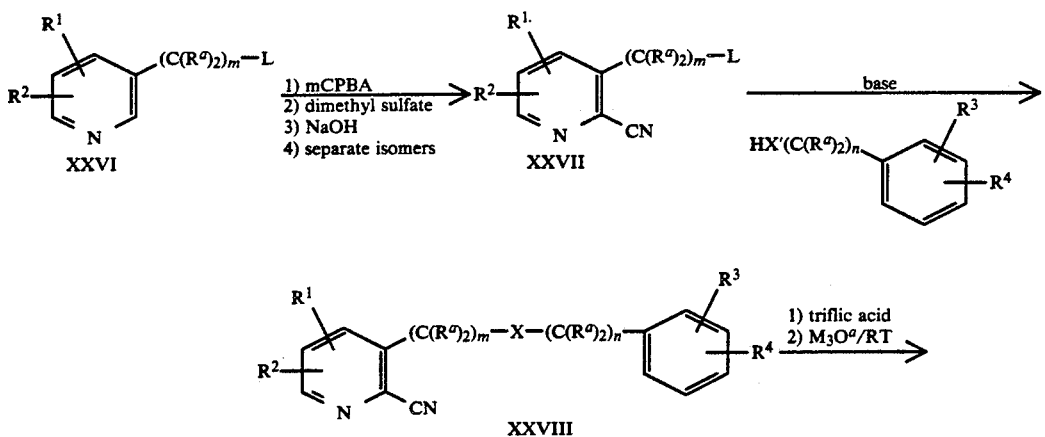

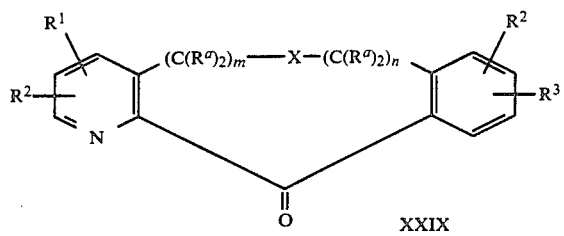

XXIX

Alternatively, compounds of the formula I, where T is a carbon atom having a double bond may be prepared by a ring closure reaction, wherein the desired cycloheptene ring is formed by treating compound XL with a super acid. Suitable super acids for this purpose include, for example, HF/BF$_3$, CF$_3$SO$_3$H (triflic acid), CH$_3$SO$_3$H/BF$_3$, etc. The reaction can be performed in the absence of, or with, an inert co-solvent such as CH$_2$Cl$_2$. The temperature and time of the reaction vary with the acid employed. For example, with HF/BF$_3$ as the super acid system the temperature may be controlled so as to minimize side reactions, such as HF addition to the exocyclic double bond. For this purpose, the temperature is generally in the range of from about +5° C. to −50° C. With CF$_3$SO$_3$H as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents.

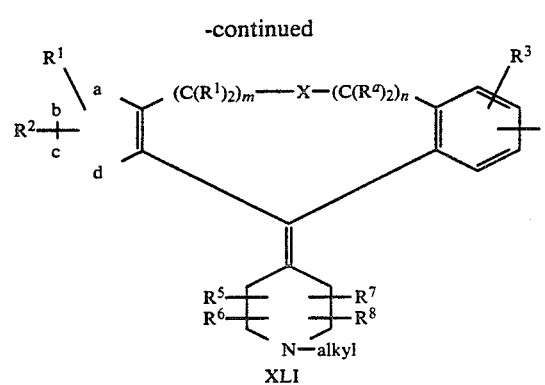

XLI

A ketone compound of formula XL may be formed by hydrolysis of XLII e.g., such as by reacting a Grignard intermediate of formula XLII with an aqueous acid (e.g., aqueous HCl). Ia in formula XLII represents chloro, bromo or iodo.

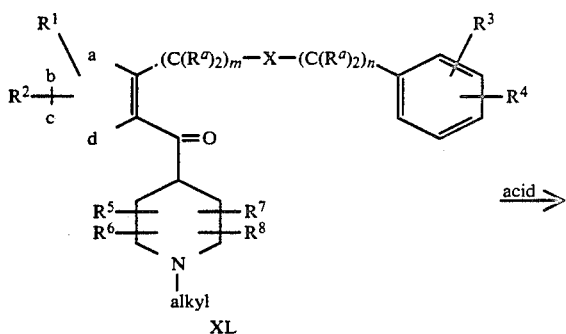

XL

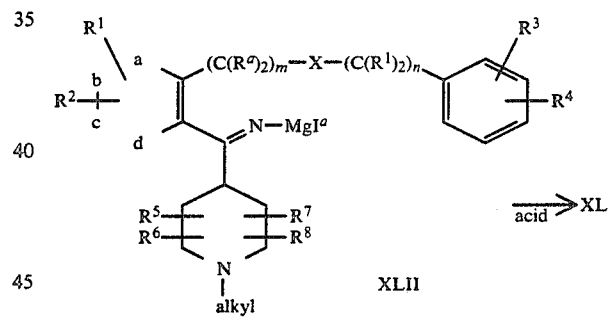

XLII

The Grignard intermediate XLII is formed by the reaction of the cyano compound XLIII with an appropriate Grignard reagent XLIV prepared from 1-alkyl-4-halopiperidine. The reaction is generally performed in an inert solvent, such as ether, toluene, or tetrahydrofuran, under general Grignard conditions e.g., temperature of from about 0° C. to about 75° C. Alternatively, other organometallic derivatives of the 1-alkyl-4-halo piperidine can be employed.

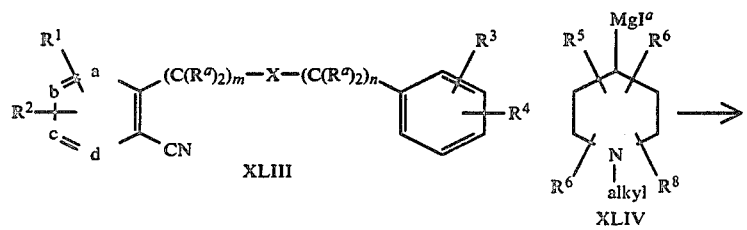

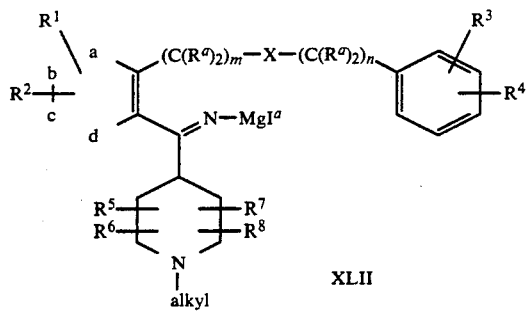

XLII

An alternative process for the formation of compounds having general structural formula I involves direct cyclization of the Compound XLV as shown below.

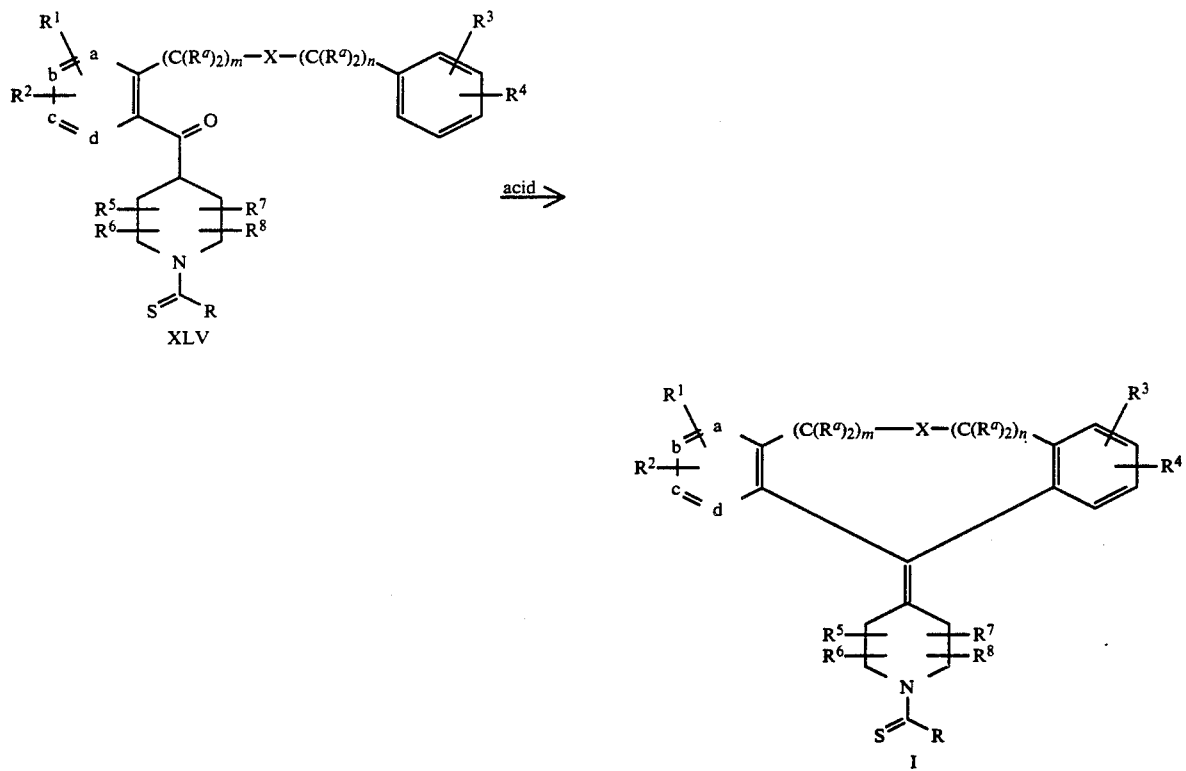

Cyclization to form the cycloheptane ring is accomplished with a strong acid (e.g., triflic, polyphosphoric, HF/BF₃), and may be performed in an inert solvent, such as ether, toluene or THF. The temperature and time may vary with the acid employed, as described in process A above.

Compounds of formula XLV where Z=O or S may be prepared by treating a compound of formula XL with an appropriate acyl halide or acyl anhydride. Most preferably this reaction is run in the presence of a good nucleophile, such as LiI, in the appropriate solvent, such as toluene, dioxane or xylene, and at a temperature ranging from 50°–150° C., preferably 100°–120° C.

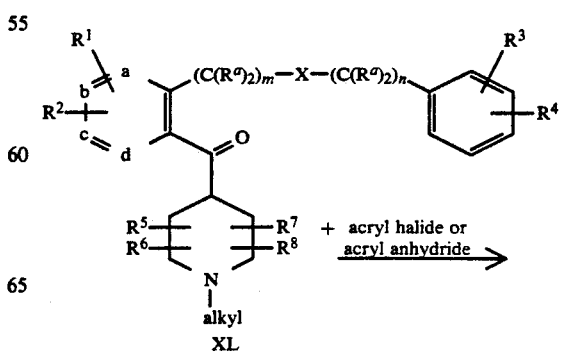

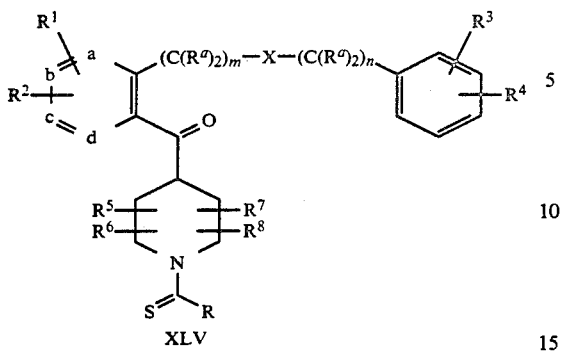

XLV

A second method of preparing compounds of formula XLV involves reacting an unsubstituted piperidylidene compound of formula XLVI with the appropriate acyl halide or acyl anhydride with or without the presence of base, such as pyridine or triethylamine. Alternatively, if L=OH in the acyl halide or acyl anhydride, then coupling of compound XLVI may require use of a conventional coupling agent, such as DCC or CDI.

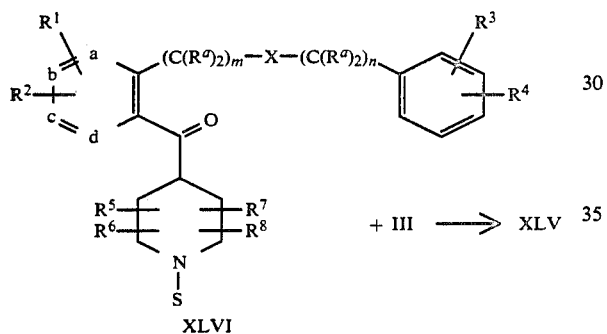

XLVI + III ⟶ XLV

Compounds of formula XLVI are produced from the corresponding carbamates of formula XLVII, via acid hydrolysis, using for example, aqueous hydrochloric acid, or base hydrolysis using for example, potassium hydroxide. Alternatively, some compounds can be prepared by treating the carbamate, formula XLVII with an organometallic reagent, such as methyl lithium or a reductive reagent, such as zinc in acid, etc., depending upon the nature of the $R^a$ group. For example, if $R^a$ is a simple alkyl group, $CO_2R^a$ may be cleaved by alkaline hydrolysis at 100° C.

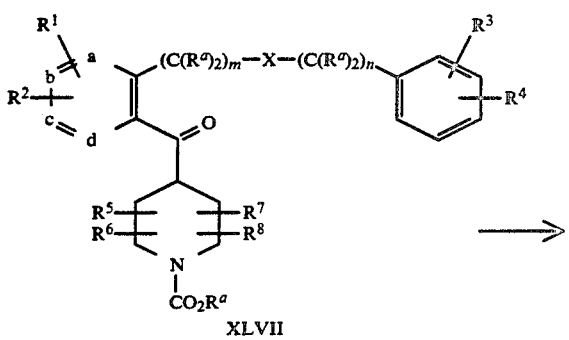

XLVII

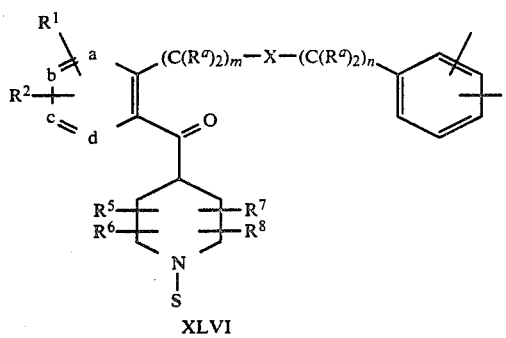

XLVI

The carbamate compounds of formula XLVII may be prepared from the appropriate alkyl compound of formula XL by treatment with a chloroformate, preferably in an inert solvent, such as toluene, with warming to approximately 80° C. Other alternate methods are available for the coversion of XL to XLVI as previously described (e.g. Von Braun reaction conditions). Compound XL may then be prepared as described above.

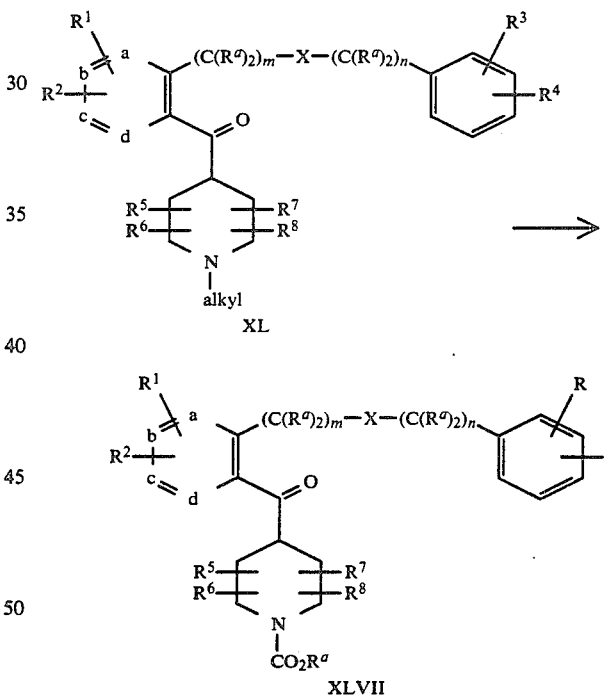

XL

XLVII

PREPARATION OF PIPERAZINE ANALOGS

Compounds of the piperazine type where T is N in formula I, are best prepared via alkylation of an appropriately substituted piperazine compound XXX with Compound XXXII containing the appropriately substituted halide (such as Cl, Br, I) or other similar leaving group (tosyloxy or mesyloxy). The reaction usually is conducted in an inert solvent such as THF or toluene, optionally with a base such as triethylamine or potassium carbonate, typically at a temperature range of ambient to reflux to produce Compound XXXIII.

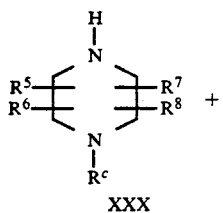

XVI

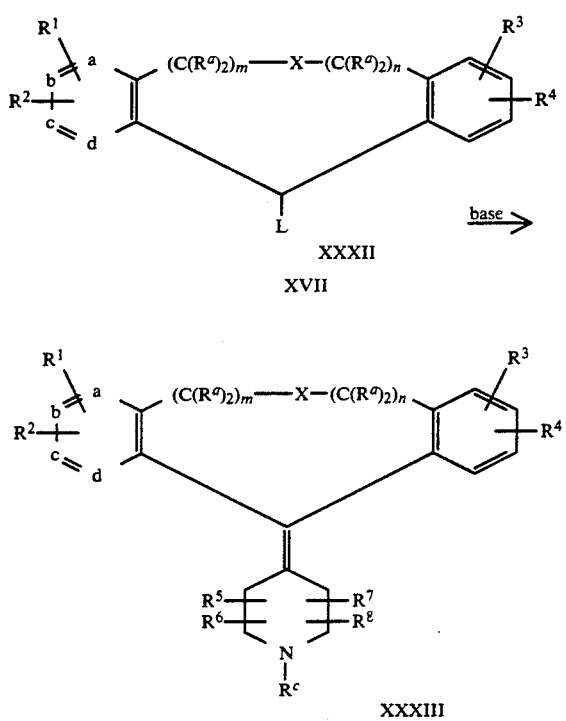

XVII

XXXIII

In this reaction $R^c$ is H, $CO_2R^b$, C(Z)R or alkyl. The preparation of the tricyclic ring structure where L is Cl is analogous of the procedure described in U.S. Pat. No. 3,409,621. When $R^c$ is C(Z)R, compounds of the invention are prepared. When $R^c$ is H, alkyl or $CO_2R^b$, the compounds are converted to compounds of the invention by processes previously described herein.

An alternative route for generating Compound XXXIII is by reductive amination of the aza ketone XXIX with the appropriately substituted piperazine.

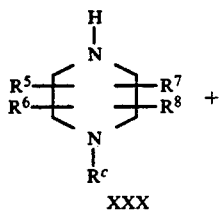

XXX

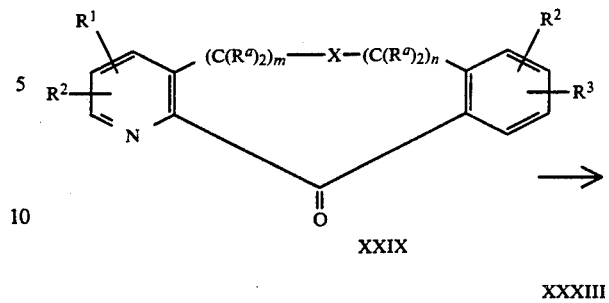

XXIX

The reaction typically is carried out in a polar solvent, such as methanol or ethanol optionally in the presence of a dehydrating agent such as 3/ molecular sieves. The intermediate Schiff base can be reduced to by employing a variety of reducing agents such as $NaCNBH_3$ or catalytic hydrogenation, for example, hydrogen over Pd/C.

When $R^c$ is C(Z)R, these are the compounds of the present invention. When $R^c$ is H, $CO_2R^b$ or alkyl, these are converted to compounds of the invention as previously described.

PREPARATION OF SINGLE BOND COMPOUNDS

Compounds where T is a carbon atom having a single bond to the tricyclic structure may be prepared by the following methods.

A. Compounds having a ketone XL may be converted to the corresponding alcohol XXIV by employing an appropriate reducing agent. The reduction can be accomplished with a variety of reducing agents (e.g. $NaBH_4$ or $LiAlH_4$) in an inert solvent such as THF or ether. Compounds of the type XL are previously described.

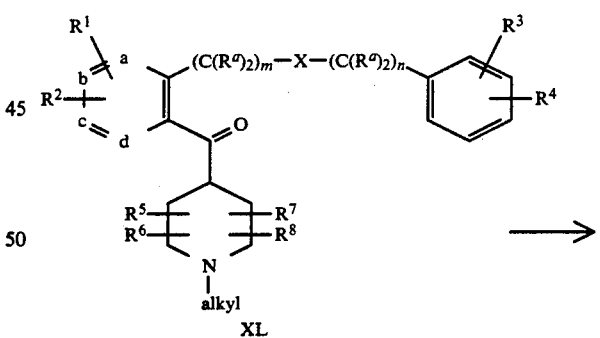

XL

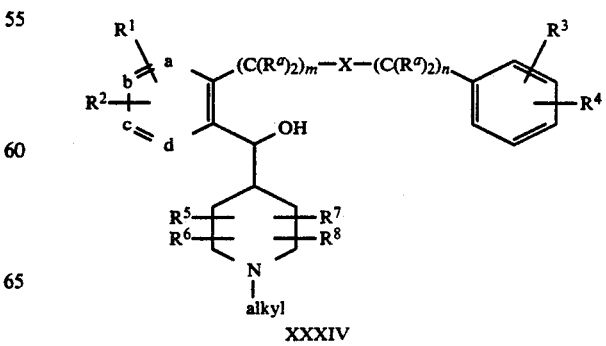

XXXIV

Compounds XXXIV may be cyclized to compound V (where T is carbon and has a single bond) via a variety of methods. For example, the cyclization can be conducted using triflic acid or PPA under conditions similar to those described for the cyclization previously described. Compound V can then be converted to compounds of the invention as previously described.

Alternatively, these compounds can be prepared via catalytic hydrogenation of the double bond between the piperidylidene carbon atom and the tricyclic ring moiety as described in U.S. Pat. Nos. 3,419,565; 3,326,924; and 3,357,986. A variety of catalysts can be used, such as Pt, Rh, Ru or Pd on various supports.

(C) A third method for the preparation of the subject compounds is by the use of the appropriately substituted Grignard reagent VIII (or other corresponding metalated reagent e.g., organolithium, etc.). Compound VIII can be reacted with compound XXXII where L is a leaving group (e.g. chloride) to provide the desired Compound XLVIII.

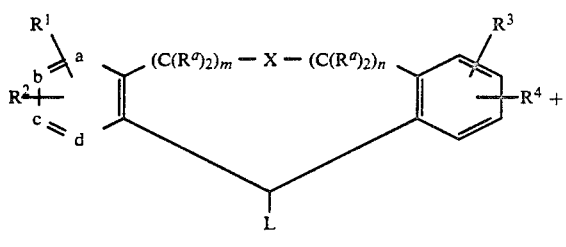

XXXII

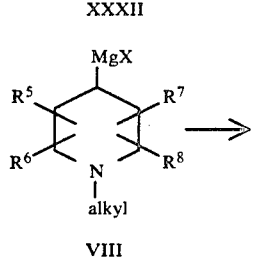

VIII

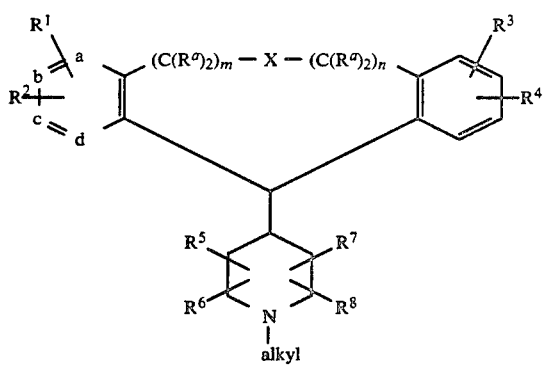

XLVIII

These reactions generally are conducted in an inert solvent such as ether, toluene, or THF at a temperature range of about −78° to about +50° C.

Alternatively, the metalating substituent and the leaving substituent could be interchanged and reacted under the same conditions to produce the same compound XLVIII.

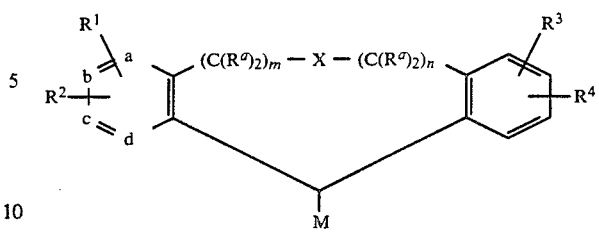

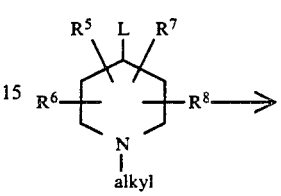

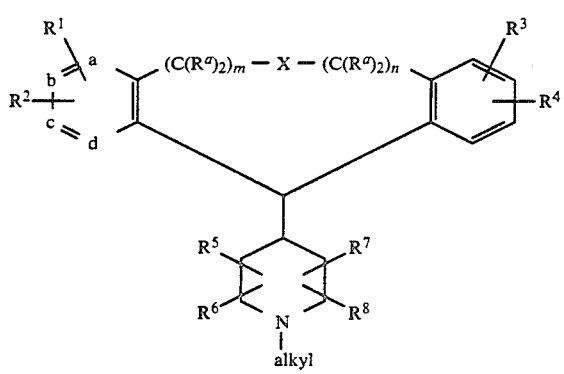

XLVIII

Compound XLVIII can be converted to compounds of the invention as previously described. Further details on these processes are described in U.S. Pat. Nos. 3,419,565; 3,326,924, 3,357,986 and in Org. Chem. 50 p. 339 (1986).

D. Alternatively, compounds of formulae XLIX and L, the preparation of which is disclosed in U.S. Pat. Nos. 3,419,565; 3,326,924; and 3,357,986, can be used to provide Compound XLVIII. This can be accomplished by reductive removal of the alcohol under a variety of conditions e.g. the methods disclosed in J.A.C.S. 104 p. 4976 (1982) and in J. Org. Chem. 50 p. 339 (1985).

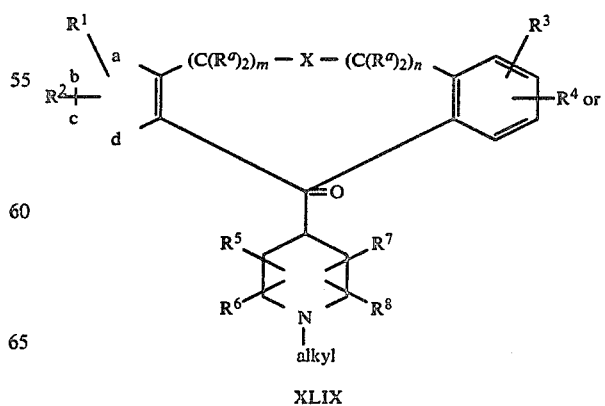

XLIX

-continued

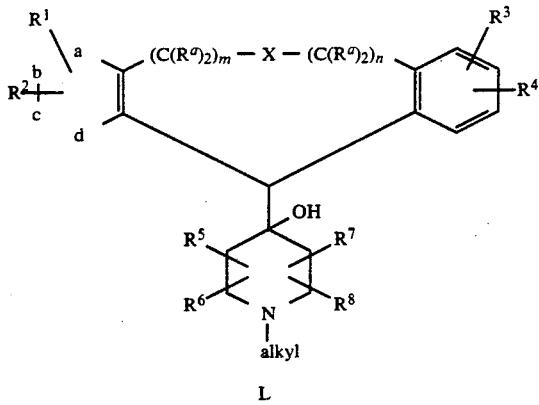

L

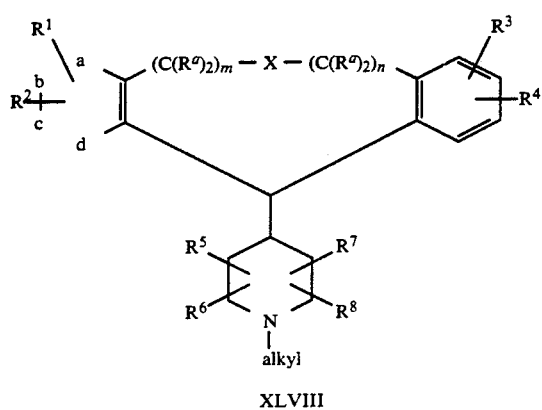

XLVIII

Compound XLVIII may be converted to compounds of the present invention as previously described.

To make a compound of the invention where Z represents sulfur, a compound of formula I where Z is oxygen is reacted with $P_2S_5$, Lawesson's reagent or another reagent capable of introducing sulfur in place of oxygen.

The reaction may take place at an elevated temperature in pyridine, toluene or another suitable solvent. Lawesson's reagent has the formula

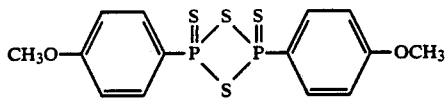

In this and other reactions, conversions of a compound of formula I (Z=O) to another compound of formula I (Z=S) are possible.

In the above processes, it is sometimes desirable and/or necessary to protect certain R and $R^1$ to $R^8$ groups during the reactions. Conventional protecting groups are operable. For example, the groups listed in column 1 of the following table may be protected as indicated in column 2 of the Table:

| Group to be Protected | Group in Protected Form |
|---|---|
| —COOH | —COOalkyl, —COObenzyl, —COOphenyl |
| NH | $NCO_2$alkyl, $NCO_2$benzyl, $NCO_2CH_2CCl_3$ |
| C=O | ![structures] |
| —OH | —O-tetrahydropyranyl, —OCH$_3$ |
| —NH$_2$ | N-succinimidyl |

Other protecting groups well known in the art also may be used. After the reaction or reactions, the protecting groups may be removed by standard procedures.

The compounds of the invention possess platelet-activating factor ("PAF") antagonistic properties. PAF is an important biochemical mediator of such processes as platelet aggregation, smooth muscle contraction (especially in lung tissue), vascular permeability and neutrophil activation. Recent evidence implicates PAF as an underlying factor involved in airway hyperreactivity. The compounds of the invention are, therefore, useful whenever PAF is a factor in the disease of disorder. This includes allergic diseases such as asthma, adult respirator distress syndrome, urticaria and also inflammatory diseases such as rheumatoid arthritis and osteoarthritis.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. PAF Antagonism Assay

In vitro Assay

Preparation of platelet-rich plasma (PRP): Human blood (50 ml) was collected from healthy male donors in an anticoagulant solution (5 ml) containing sodium citrate (3.8%) and dextrose (2%). Blood was centrifuged at 110×g for 15 min. and the supernatant PRP carefully transferred into a polypropylene tube. Platelet-poor-plasma (PPP) was prepared by centrifuging PRP at 12,000×g for 2 min. in a Beckman Microfuge B. PRP was used within 3 hours of drawing the blood.

Platelet Aggregation Assay: When an aggregating agent such as PAF is added to PRP, platelets aggregate. An aggregometer quantifies this aggregation by measuring light (infra-red) transmission through PRP and comparing to PPP. The aggregation assays were performed using a dual-channel aggregometer (Model 440, Chrono-Log Corp., Havertown, Penna.) PRP (0.45 ml)

in aggregometer curettes was continually stirred (37° C.). Solutions of test compounds or vehicle were added to the PRP, and after incubation for 2 min., 10–15)1 aliquots of PAF solution were added so as to achieve a final concentration of $1-5\times10^{-8}$M. Incubations were continued until the increase in light transmission reached a maximum (usually about 2 min). Values for inhibition were calculated by comparing maximal aggregation obtained in the absence and the presence of the compound. For each experiment, a standard PAF antagonist, such as alprazolam, was used as a positive internal control. The inhibitory concentration ($IC_{50}$) is the concentration of compound in micromoles at which 50% of the aggregation is inhibited, as measured by the light transmission through each sample of PRP as compared to PPP. The test results are shown below in Table I.

Since PAF is a known bronchoconstrictive agent in mammals, PAF antagonism can be evaluated by measuring inhibition by the compounds of the invention in PAF-induced ronchoconstriction in guinea pigs.

B. PAF-Induced Bronchospasm in Guinea Pigs

In Vivo Assay

Non-sensitized guinea pigs were fasted overnight, and the following morning were anesthetized with 0.9 ml/kg i.p. of dialurethane (0.1 g/ml of diallybarbituric acid, 0.4 g/ml of ethylurea and 0.4 g/ml of urethane). The trachea was cannulated and the animals were ventilated by a Harvard rodent respirator at 55 strokes/min. with a stroke volume of 4 ml. A side arm to the tracheal cannula was connected to a Harvard pressure transducer to obtain a continuous measure of intratracheal pressure, which was recorded on a Harvard polygraph. The jugular vein was cannulated for the administration of compounds. The animals were challenged i.v. with PAF (0.4 ug/kg in isotonic saline containing 0.25% BSA) and the peak increase in inflation pressure that occurred within 5 min. after challenge was recorded. Test compounds were administered either orally (2 hrs. prior to PAF as a suspension in 0.4% methylcellulose vehicle) or intravenously (10 min. prior to PAF as a solution in dimethylsulfoxide.

The compounds of the invention also possess antihistaminic properties which may be assessed by test procedure C below. Test procedure C, "Prevention of histaminic-induced lethality" demonstrates basic anti-histaminic activity of representative compounds of structural formula I. Protection against histamine lethality is indicative of strong antihistaminic properties.

Test procedures D, E and F demonstrate the extent of CNS activity induced by the compounds of the invention. The presence of strong CNS activity indicates a high probability of sedation caused by the compounds, a typically undesirable side effect of antihistiamines. Consequently, a low level of CNS activity is preferred in most circumstances.

C. Antihistamine Activity Assay

Prevention of Histamine-Induced Lethality in Guinea Pigs. The compounds may also be evaluated for antihistamine activity by their ability to protect female albino guinea pigs (250–350 g) against death induced by the intravenous injection of histamine dihydrochloride at 1.1 mg/kg, which is approximately twice the $LD_{99}$. Doses of the antagonists are administered orally to separate groups of fasted animals 1 hour prior to the challenge with histamine and protection from death recorded for 30 minutes after histamine. $ED_{50}$ values were determined for each drug by probit analysis.

CNS Activity Assay

D. Antagonism of Physostigmine Lethality. The physostigmine-induced lethality test is indicative of CNS activity and the test described is a modification of the technique reported by COLLIER et al., *Br. J. Pharmac.*, 32, 295–310 (1968). Physostigmine salicylate (1.0 mg/kg s.c.) produces 100% lethality when administered to mice grouped 10 per plastic cage ($11\times26\times13$ cm). Test agents were administered orally 30 minutes prior to physostigmine. The number of survivors were counted 20 minutes after physostigmine administration.

E. Antagonism of Acetic Acid Writhing. The acetic acid writhing test is a second test useful for determining CNS activity, and is essentially that described by HENDERSHOT and FORSAITH, *J. Pharmac. Exp. Ther.*, 125, 237–240 (1959), except that acetic acid rather than phenylquinone was used to elicit writhing. Mice were injected with 0.6% aqueous acetic acid at 10 mg/kg i.p. 15 minutes after oral administration of the test drug. The number of writhes for each animal was counted during a 10 minute period starting 3 minutes after acetic acid treatment. A writhe was defined as a sequence of arching of the back, pelvic rotation and hind limb extension.

F. Antagonism of Electro-Convulsive Shock (ECS). The ECS test is a third test useful for determining CNS activity. For the ECS test, a modification of the method of TOMAN et al., *J. Neurophysiol.*, 9, 231–239 (1946), was used. One hour after oral administration of the test drug or vehicle, mice were administered a 13 mA, 60 cycle a.c. electroconvulsant shock (ECS) for 0.2 seconds via corneal electrodes. This shock intensity produces tonic convulsions, defined as extension of the hind limbs, in at least 95% of vehicle-treated mice.

Of the above test procedures for measuring CNS activity, the physotigmine-induced lethality test is believed to be a major index of non-sedating characteristics potency which is believed to contribute to sedative activity.

In the Table I below PAF antagonism data are presented for previously known compounds and for compounds of the present invention.

TABLE I

| Compound | Dose | Percent PAF Antagonism |
|---|---|---|
| 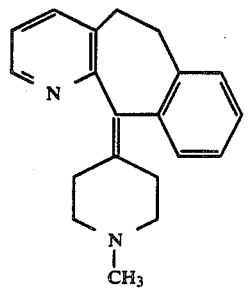 | >50* | 50% |

TABLE I-continued

| Compound | Dose | Percent PAF Antagonism |
|---|---|---|
| (8-chloro-benzocycloheptapyridine with piperidine N-CO-OC₂H₅) | >175* | 50% |
| (pyridine fused cyclopentane-indane with piperazine N-acetyl) | 50 μM | 13% |
| (pyrano-pyridine with phenyl, piperidine N-acetyl) | 50 μM / 25 μM | 47% / 32% |
| (pyrano-pyridine with phenyl, piperidine N-CHO) | 50 μM | 20% |
| (pyrano-pyridine with phenyl, piperidine N-acetyl) | 50 μM / 12 μM | 92% / 50% |

TABLE I-continued

| Compound | Dose | Percent PAF Antagonism |
|---|---|---|
| (pyridine-SOₙ-phenyl with piperidine N-acetyl) | 5.5 μM, n=0; 32 μM, n=1; 3 μM, n=2; 12 μM | 50%; 50%; 50%; 50% |
| (pyridine N-oxide SO₂ phenyl with piperidine N-acetyl) | 27 μM | 50% |
| (chloro-pyrano-pyridine with piperidine N-acetyl) | 50 μM / 5 μM | 100% / 52% |
| (thio-pyrano-pyridine with piperidine N-acetyl) | 50 μM / 5 μM | 100% / 47% |
| (dihydroacridine with piperidine N-acetyl) | 50 μM / 5 μM | 100% / 79% |

*previously known compounds

As seen from the data in Table I, the compounds of structural formula I exhibit PAF antagonist activity. Consequently, it is within the scope of this invention to use each of these compounds when clinically appropriate.

For preparing pharmaceutical composition from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient on a weight/weight basis. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.01 mg to 2000 mg, more preferably from about 1 mg. to 100 mg, according to the particular application. The appropriate dosage can be determined by comparing the activity of the compound with the activity of a known PAF antogonist.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptoms being treated. A typical recommended dosage regiment for oral administration is from 10 mg to 2000 mg/day preferably 10 to 750 mg/day, in two to four divided doses to achieve relief of the symptoms. The dosage ranges for the treatment of allergy and inflammation are generally considered to be the same. Hence oral dosage ranges will be similar, injectable dosage ranges will be similar, etc.

The following examples are intended to illustrate, but not to limit, the present invention.

PREPARATIVE EXAMPLE 1

A.

1-Methyl-4-(10H-[1]benzothiopyrano[3,2-b]-10-hydroxypyridinyl]piperidine

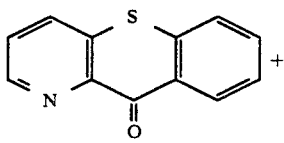

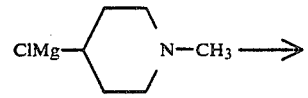

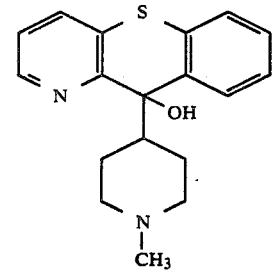

Suspend benzo[b]thiopyrano[2,3-b]-pyridin-10-one (1.3 g; 6.1 mmole) in dry tetrahydrofuran ("THF") (30 ml) at room temperature and under an argon atmosphere. Add N-methyl-4-piperidinyl magnesium chloride (1.2 eq., 4.8 ml of 1.5M reagent in THF), forming a dark solution. Stir at room temperature for 1 hour.

Quench the reaction with concentrated NH$_4$Cl and extract with ethyl acetate. Wash the organic portions with brine and dry over Na$_2$SO$_4$. Remove the solvent and chromatograph the resultant liquid (5%→10% CH$_3$OH/NH$_3$ in CH$_2$Cl$_2$) to produce a yellowish solid which may be crystallized from pentane (0.80 g).

B.
1-Methyl-4-(10H-[1]benzothiopyrano[3,2-b]pyridin-10-ylidene)piperidine

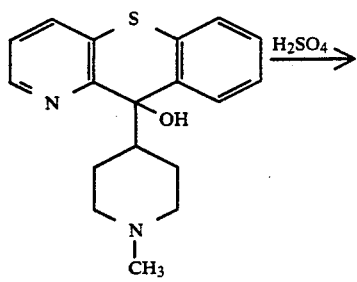

Warm the title compound of part A above (780 mg) in H₂SO₄ (85%, 20 ml) to 105° C. in an oil bath for 20 minutes. Pour the reaction mixture into ice water and basify with NaOH (25%). Extract with CH₂Cl₂ and wash the combined organic portions with brine. Dry over Na₂SO₄ to produce a yellowish glass (408 mg).

Purify with flash chromatography over (10%T15% CH₃OH in CH₂Cl₂) to produce a yellowish glassy solid (290 mg).

C.
1-Cyano-4-(10H-[1]benzothiopyrano[3,2-b]pyridin-10-ylidene)piperidine

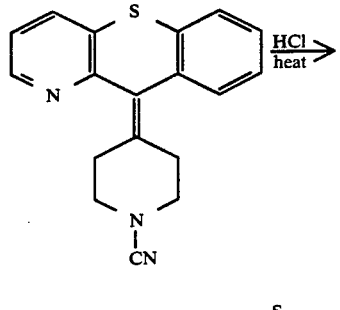

Add the title compound of part B above (291 mg) to a solution of cyanogen bromide (158 mg, 1.5 eq) in dry benzene (8.5 ml) at room temperature, and stir for 3 hours.

Remove the solvent under high vacuum to produce a solid and flash chromatograph (5% CH₃OH in CH₂Cl₂) to produce the title compound as a yellowish solid (220 mg, m.p. 192°–193° C.).

D.
1-Aminocarbonyl-4-(10H-[1]benzothiopyrano[3,2-b]pyridin-10-ylidene)piperidine and
4-(10H-[1]benzothiopyrano[3,2-b]pyridin-10-ylidene)-piperidine Reflux a mixture of the title compound of part C above (210 mg) and 29% aq HCl (20 ml) for 24 hours. Pour the reaction mixture onto ice and basify with 25% aqueous NaOH. Extract the mixture with CH₂Cl₂ (2×200 ml) and wash the combined organic portions with brine. Dry over Na₂SO₄, filter and remove the solvent to yield a glassy solid.

Chromatograph on SiO₂ (230–400 mesh), eluting with 10%T15% CH₃OH in CH₂Cl₂ to yield the title compounds in two fractions, fraction 1 containing the N—H compound 1A as a yellowish solid (146 mg, m.p. 162°–163° C.), and fraction 2 containing the aminocarbonyl substituted compound 1B as an off-white solid (32 mg, 185°–187° C.).

PREPARATIVE EXAMPLE 2

A.
1-Methyl-4-(10H-[1]benzopyrano[3,2-b]pyridin-10-ylidene)piperidine

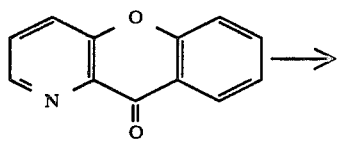

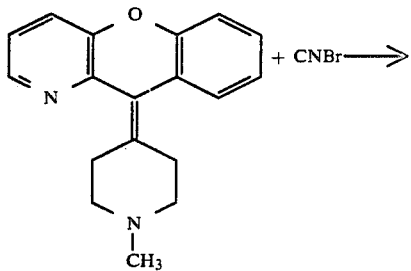

Prepare 1-methyl-4-(10H-[1]benzopyrano[3,2-b]pyridin-10-ylidene)piperidine, as described in U.S. Pat. No. 3,803,153.

B.
1-Cyano-4-(10H-[1]benzopyrano[3,2-b]pyridin-10-ylidene)piperidine

Stir a solution of cyanogen bromide (22.9 g, 0.196 m) in dry benzene (300 ml) at room temperature, and add a solution of the title compound of part A above (54.5 g, 0.196M) in benzene (300 ml).

Filter the resulting solution after 3 hr. and concentrate to dryness to produce an off-white solid (44.0 g, m.p. 172°–175° C.).

Recrystallize the product from acetonitrile to afford the title compound.

C. 4-(10H)-[1]benzopyrano[3,2-b]pyridin-10-ylidene)piperidine

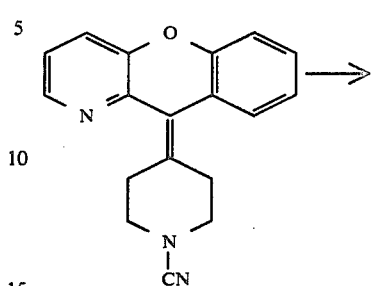

Reflux a mixture of the title compound from part B above (44.0 g, 0.152M), glacial acetic acid (1140 ml), conc. HCl (115 ml) and H₂O (760 ml) for 20 hours. Remove excess acetic acid and H₂O under reduced pressure, cool and basify with Na₂CO₃. Extract with chloroform and dry over Na₂SO₄. Concentrate to dryness and chromatograph on silica gel using acetonitrile to produce the title compound (27.0 g, m.p. 158°–160° C.).

PREPARATIVE EXAMPLE 3

A. 3-(3-phenylpropyl)pyridine

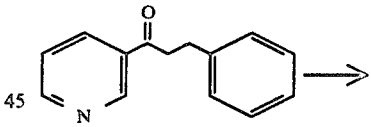

Heat a mixture of 2-phenylethyl 3-pyridinyl ketone (19.5 g, 0.092M), NaOH (8.0 g), hydrazine hydrate (8 ml, 85% in H₂O) and diethylene glycol (125 ml) to 240° C. for 4 hours.

Extract with benzene (1X), then diethyl ether (1X). Wash the combined organic extracts with H₂O (3X), remove the solvent and distill to produce the title compound (15.8 g, b.p. 130°–131° C. at 2 mmHg).

B. 3-(3-phenylpropyl)pyridine-N-oxide

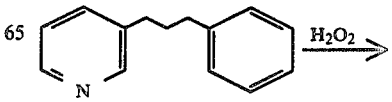

-continued

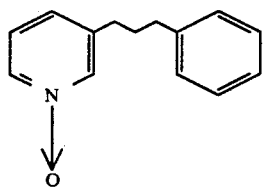

Add cold H₂O₂ (101 ml, 30%) to a cold solution of the title compound from part A above (166 g, 0.84M) in CH₃CO₂H (252 ml).

Heat to 60° C. for 24 hours and pour into ice water. Basify with NH₄OH, bringing the total volume to 2.0L. The product separates out as an oil, which solidifies upon cooling. Filter and dissolve the filtrate in CHCl₃.

Remove the solvent and crystallize the product from benzene/hexane to produce the title compound (63.0 g, m.p. 34°–35° C.).

C. 2-Cyano-3-(phenyl-n-propyl)pyridine

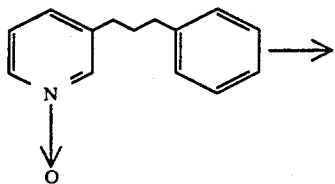

Add dimethyl sulfate (76 g, 0.6M) to the title compound from part B above (171.5 g) and stir on a steam bath for 3 hours. Add H₂O (200 ml) and cool the solution, then add the solution dropwise to a solution of NaCN (92 g) in H₂O (260 ml) at 0° C. under a N₂ atmosphere. Allow the solution to remain at 0° C. for 4 hours, then stir the mixture for 12 hours at room temperature, while maintaining the reaction under an N₂ atmosphere. Extract the resultant brownish solution with CHCl₃. Concentrate the combined organic portions and purify via distillation. Crystallize the title compound from the appropriate fractions using benzene/pet ether (34.0 g, m.p. 50°–52° C.).

D. 12H-benzo[b]-5,6,7,12-tetrahydrocycloocta[2,3-b]pyridin-12-one

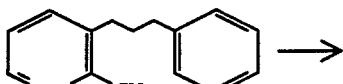

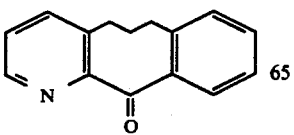

Stir the title compound from part C above (5.0 g) with polyphosphoric acid (250 g) while heating to 240° C., then reduce heat to 220° C. and maintain for 2 hours.

Pour the reaction mixture into ice water and basify with NaOH. Extract with diethyl ether and remove the solvent to form the title compound in crude form (4.0 g, m.p. 141°–145° C.) which may be recrystallized from 2-butanone to produce the title compound as a white solid (m.p. 153°–155° C.).

E. 1-Methyl-4-(5,6,7,12-tetrahydrobenzo[6,7]cycloocta[1,2-b]-2-hydroxypyridinyl)piperidine

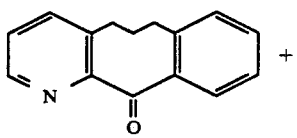

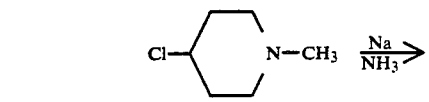

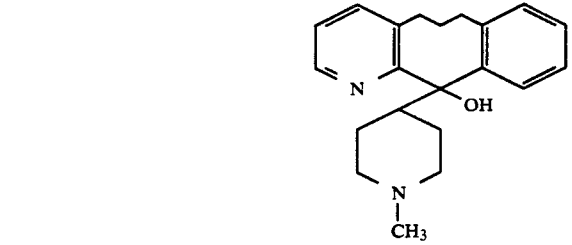

Dissolve sodium (2.7 g, 0.12M) in NH₃ (200 ml) and stir for 20 minutes. Add the title compound from part D above, (13 g, 0.058M) in THF (105 ml) slowly and stir for 5 minutes. Add a solution of 4-chloro-1-methyl-piperidine (7.8 g, 0.058M) in THF (25 ml) and continue stirring.

Add NH₄Cl (5.0 g) and NH₃ (75 ml) and continue stirring for an additional 2 hours.

Concentrate the mixture to dryness, then partition over water and benzene. Extract with additional benzene. Remove the solvent to form a viscous tan residue.

Triturate the tan residue with pet ether and isopropyl ether. Cool the solution and decant off the liquids from the precipitate to obtain the title compound as a white solid (5 g, m.p. 122°–124° C.).

F. 1-Methyl-4-(5,6,7,12-tetrahydrobenzo[6,7]cycloocta-[1,2-b]pyridin-12-ylidene)piperidine

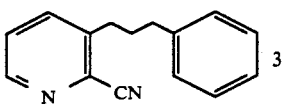

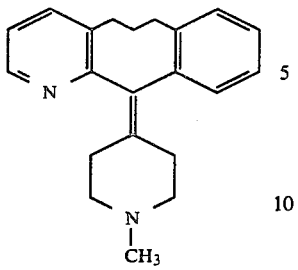

Combine the title compound from part E above (1.413 g) with CH₃CO₂H (12 ml), acetyl chloride (7 ml) and acetic anhydride (3.5 ml) and heat to 100° C. under an N₂ atmosphere.

After 3 hours concentrate the mixture in vacuo and pour the residue into NaOH (1N). Extract with CH₂Cl₂ (3X). Combine the organic portions, dry over MgSO₄, filter and rotary evaporate to dryness.

Purify by flash chromatography (5% CH₃OH/NH₃ in CH₂Cl₂) to produce the title compound which may be crystallized from pentane (1.014 g).

G. 1-(1,1,1-Trichloroethoxycarbonyl)-4-(5,6,7,12-tetrahydrobenzo[6,7]cycloocta[1,2-b]pyridin-12-ylidene)piperidine

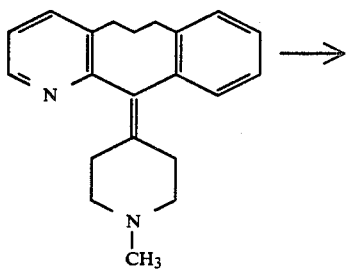

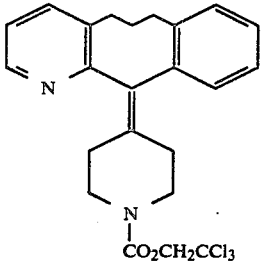

Combine the title compound from part F above (1.008 g, 3.31 mmol) with (CH₃CH₂)₃N (0.70 ml) and dry toluene (30 ml) at 90° C. under an argon atmosphere. Add dropwise 2,2,2-trichloroethylcarbonyl chloride (1.80 ml) over 20 minutes. Maintain the temperature at 90° C. for 1.67 hours, then cool to room temperature and pour into aqueous NaOH (1N).

Extract the reaction mixture with CH₂Cl₂ (3X), combine the organic portions and dry over MgSO₄.

Filter and rotary evaporate to dryness.

Purify by flash chromatography (CH₃OH 2% in CH₂Cl₂) and combine appropriate fractions to obtain the title compound.

H. 4-(5,6,7,12-tetrahydrobenzocycloocta[1,2]pyridin-12-ylidene)piperidene

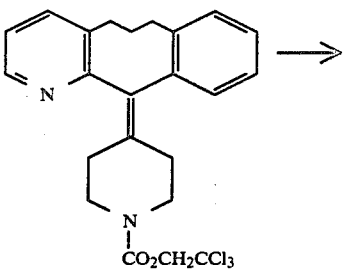

Combine the title compound from part G above and glacial acetic acid (20 ml) under an N₂ atmosphere at 90°-90° C. with zinc dust (2.12 g).

After 3 hours, cool the reaction to room temperature, filter and rotary evaporate to dryness. Basify the residue with NaOH (1N) and extract with CH₂Cl₂ (4X). Combine the organic portions, dry over MgSO₄, filter and rotary evaporate to dryness. Purify by flash chromatograph (5%T7% CH₃OH/NH₃ in CH₂Cl₂) and collect the appropriate fractions to yield the title compound as a glass (603 mg).

PREPARATIVE EXAMPLE 4

A. 2-Cyano-3-(bromomethyl)pyridine

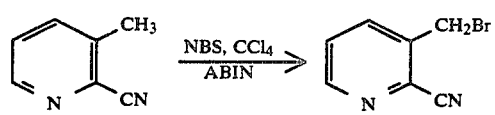

Combine 2-cyano-3-methylpyridine (11.8 g), N-bromosuccinimide ("NBS") (26.8 g, 1.0 eq) and aza(bis-)isobutyronitrile ("ABIN") (180 mg) in dry CCl₄ (300 ml). Reflux the mixture.

Pour the mixture into water, basify with NaOH and extract with CH₂Cl₂. Wash the organic portion with water, dry, filter and concentrate to obtain a liquid. Chromatograph the product, eluting with diethyl ether/hexane (30%). Combine the appropriate fractions to obtain the mono bromo compound (5.01 g) as a yellowish solid.

B. 2-Cyano-3-(3-chlorophenoxymethyl)pyridine

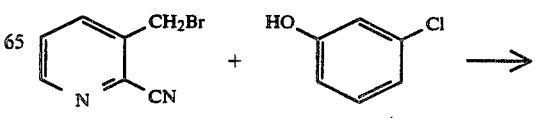

-continued

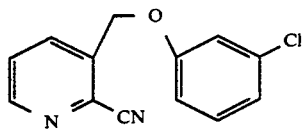

Stir a solution of the title compound of part A above (0.71 g, 3.6 mmol), NaI (54 mg, 0.1 eq) and Cs2CO3 (1.17 g, 1.0 eq) in dry acetone (17 ml, dried over MgSO4) at room temperature for 5 minutes, then add 3-chlorophenol (463 mg) via a syringe.

Reflux over an oil bath for 4.5 hrs.

Filter and wash the filtrate with dry acetone. Concentrate the filtrate, suspend in diethyl ether, and refilter to obtain a brown solid which is the title compound in crude form. Triturate with pentane, and resuspend in diisopropyl ether (40 ml) with charcoal, and heat on a steam bath.

Filter and evaporate the solvent to obtain the title compound, which crystallizes to form a white solid (640 mg, m.p. 70°-72° C.).

C.
8-Chloro-5,11-dihydro[1]benzoxepino[4,3-b]pyridin-11-one

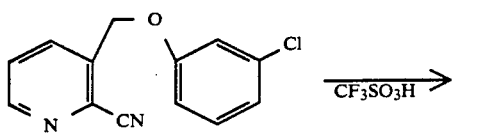

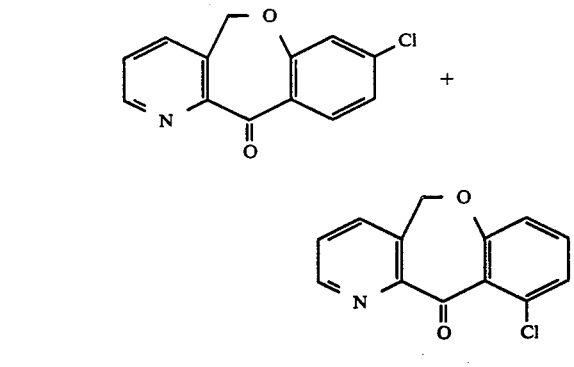

Stir the title compound from part B above (6.1 g) in CF3SO3H (60 ml) at room temperature for 3 hours. Upon completion, quench with H2O and conc. HCl (30% and continue stirring for 0.5 hours.

Warm to 35° C. for 0.5 hours. Basify with NaOH (25%) and extract with CH2Cl2(2X). Wash with brine (2X), filter and dry over Na2SO4.

Triturate the resulting semisolid (6.35 g) with diisopropyl ether and separate the isomers via flash chromatography (3% EtoAc in hexanes). Combine the appropriate fractions to obtain the title compound as a solid (4.902 g, m.p. 139.5°-140.5°), and the 10-chloro compound as a solid (462 mg, m.p. 100°-100.5° C.).

D.
1-methyl-4-(8-chloro-11-hydroxy-5,11-dihydro[1]benzoxepino[4,3b]pyridinyl)piperidine

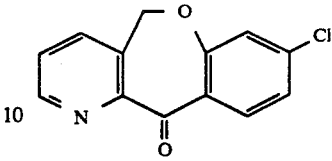

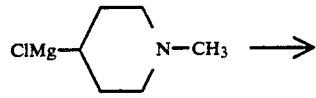

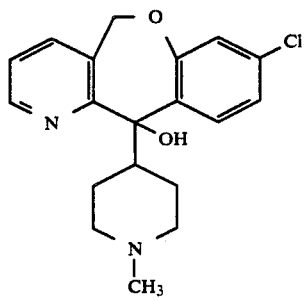

Slowly add a solution of the title compound from part C above (3.47 g) in dry tetrahydrofuran ("THF") (37 ml) to the grignard reagent (11.9 ml, 1.2M) and stir at room temperature for 0.5 hrs.

Quench the reaction with ice and NH4Cl. Extract the solution with CH2Cl2 (2X), dry, filter and concentrate to obtain the title compound. Chromatograph the product on silica gel (5%T7.5% CH3OH/NH3 in CH2Cl2) to obtain the title compound as a glass (2.56 g).

E.
1-Methyl-4-(8-chloro-5,11-dihydro[1]benzoxepin[4,3-b]pyridin-11-ylidene) piperidine

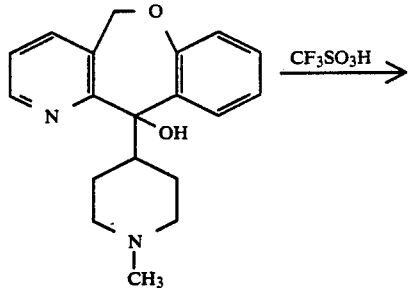

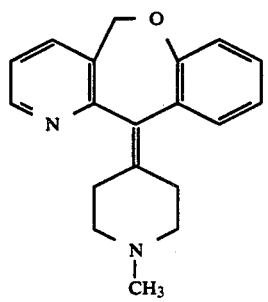

Stir the title compound from part D above (934 mg) in CF$_3$SO$_3$H (20 ml) at room temperature for 15 min. Raise temperature to 45° C. on an oil bath and maintain for 1.25 hrs. Cool to room temperature and pour the mixture into ice water. Basify with dilute NaOH, and extract with CH$_2$Cl$_2$ (2X). Wash with brine (1X) and dry over Na$_2$SO$_4$ to obtain the title compound as a brown glass.

Purify by combining with charcoal in ethyl acetate, then filter and remove solvent to obtain a yellowish brown solid.

Recrystallize from ethyl acetate and diisopropyl ether to obtain the title compound as an off-white solid (540 mg, m.p. 168°–170° C.).

F. 1-Ethoxycarbonyl-4-(8-chloro-5,11-dihydro[1]benzoxepino[4,3-b]pyridin-11-ylidene)piperidine

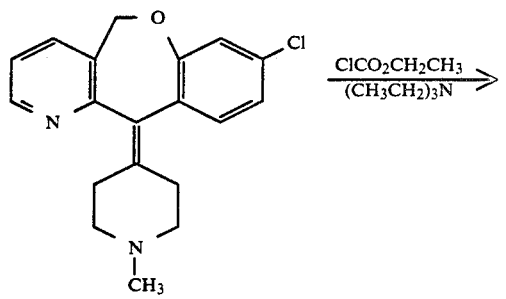

Dissolve the title compound from part E above (474 mg, 1.45 mmol) in toluene (10 ml) and add (CH$_3$CH$_2$)$_3$N (0.656 ml). Warm and maintain the reaction at 80°–85° C. and slowly add ClCO$_2$CH$_2$CH$_3$ (1.242 ml). Maintain the reaction at 80°–85° C. while stirring for 3 hours.

Quench the reaction with H$_2$O and extract with ethyl acetate (2×100 ml). Wash with brine, separate and dry over Na$_2$SO$_4$. Remove the solvent and purify via flash chromatography, eluting with ethyl acetate in hexane (40T60%) to yield the title compound as an off-white solid, which may be purified by trituration with pentane and diisopropyl ether (428 mg, m.p. 118°–120° C.).

G. 4-(8-Chloro-5,11-dihydro[1]benzoxepino[4,3-b]pyridin-11-ylidene)piperidine

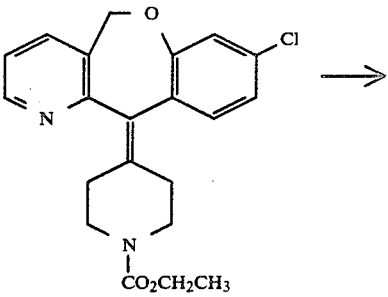

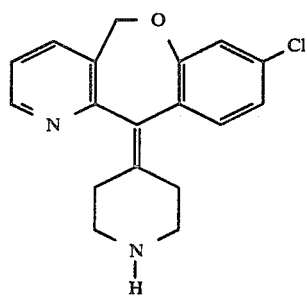

Dissolve the title compound from part F above (333.8 mg) in CH$_3$CH$_2$OH (5 ml) and add 14% aqueous KOH. Reflux under an argon atmosphere for 19 hours.

Quench the reaction with H$_2$O and extract with CH$_2$Cl$_2$ (3×100 ml). Wash with brine (1×100 ml), dry over Na$_2$SO$_4$ and filter. Remove the solvent to yield a glassy off-white solid.

Recrystallize with ethyl acetate/diisopropyl ether to yield the title compound as a white powder. (161.5 mg, m.p.. 166°–176° C.).

PREPARATIVE EXAMPLE 5

A. 1,2,6-trimethyl-4-chloropiperidine

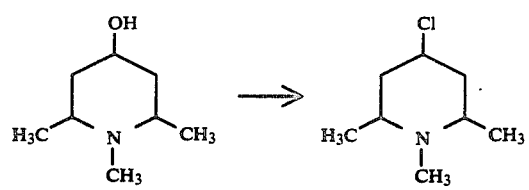

The starting material, 1,2,6-trimethyl-4-piperidinol, may be prepared by the method disclosed in *Archi Kem*, Volume 27, pages 189-192 (1955). To a cooled (ice-bath) solution of 1,2,6-trimethyl-4-piperidinol (12.2 g, 85.3 mmol) in 120 mL of dry benzene is slowly add thionylchloride (17 mL, 233 mmole). The dark reaction mixture is warmed to 70° C. for 20 min. The reaction is cooled and then suspended in water followed by filtration. The filtrate is extracted once with diethylether. The aqueous layer is separated and the basified with 30% NaOH solution. The product is then extracted twice with CH$_2$Cl$_2$, washed once with brine, dried (Na$_2$SO$_4$), filtered and the solvent removed to produce a crude brown liquid which is distilled (2–4 mmHg, 62°–64° C.) to give the title compound (8.0 g).

B.
2,6-Dimethyl-4-(10H-[1]benzothiopyrano[3,2-b]pyridin-10-ylidene)piperidine

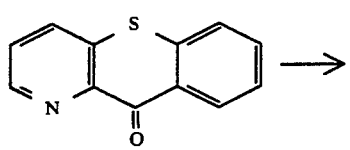

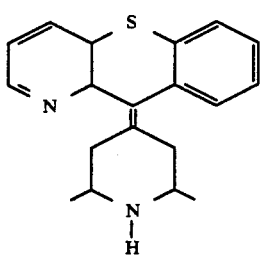

Slowly drip the chloride, 1,2,6-trimethyl-4-chloropiperidine, (4.2 g, 26 mmol) into a solution of dry THF (18 mL) containing Mg (633 mg, 26.3 mm). The Grignard reagent is formed after heating for 6 hours at 70° C.

Add the Grignard to the appropriate ketone in Preparative Example 1 and convert to the final intermediate product as described therein, thereby producing the title compound.

PREPARATIVE EXAMPLE 6

A. 3,5-DIMETHYLPYRIDINIUM N-OXIDE

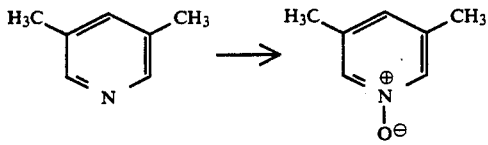

Slowly add a solution of 285 mL (1.31 mol) of 35% peracetic acid to a stirred solution of 149 g (1.39 mol) of 3,5-dimethylpyridine and maintain at 85° C. during addition. Allow the temperature of the mixture to drop to about 35° C.

After partial removal of 185 ml of acetic acid via distillation under vacuum, wash with NaHSO$_4$ solution and then neutralize with 10% NaOH solution to pH of about 7. Extract the product with CH$_2$Cl$_2$ to obtain the title compound as a white solid (142 g)

B. 1-METHOXY-3,5-DIMETHYLPYRIDINIUM METHYL SULFATE

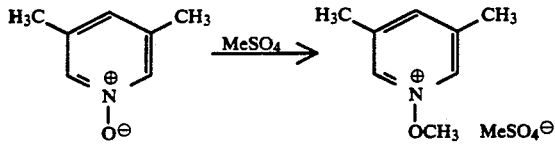

Slowly add dimethylsulfate (42.0 g, 0.33 mol) to a mechanically stirred solid of 41.0 g (0.33 mol) of 3,5-dimethylpyridinium N-oxide. Heat the mixture on a steam bath for 1 hr. Apply vacuum while cooling to produce the title compound as a brownish solid.

C. 2-CYANO-3,5-DIMETHYLPYRIDINE

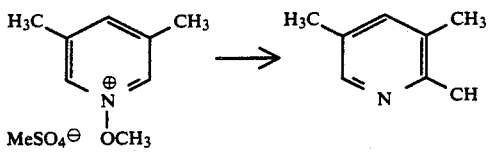

Cool a solution of sodium cyanide (49.0 g, 0.999 mol, 3.0 eq.) in 135 mL of water to 0° C., (air free) and drip 1-methoxy-3,5-dimethyl pyridinium methyl sulfate (83.0 g, 0.33 mol) in 100 mL water (air free) over 1¼ hr., keeping the temperature below 3° C. Filter the mixture and wash with water to give 40 g of the title compound which may be recrystallized from isopropyl ether and pentane (4:1) (m.p. 61°–62° C.).

D.
N-(1,1-dimethylethyl)-3,5-dimethyl-2-pyridinecarboxamide

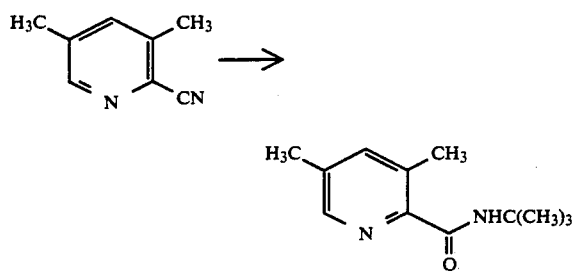

Stir a solution of 2-cyano-3,5-dimethylpyridine (20.3 g, 0.153 mol) in 100 mL of acetic acid and 20 mL of conc. sulfuric acid over 10 minutes. Add t-butanol (20 ml.) over an additional 15 minutes. Warm the solution to 75° C. and maintain for 30 minutes. Cool to room temperature and basify with 25% NaOH. Extract the product (3X) with ethyl acetate (600 mL). Combine the organic portions and wash (1X) with brine. Dry (Na$_2$SO$_4$), filter and concentrate in vacuo to produce the title compound as a yellowish oil (31.26 g).

E.
N-(1,1-DIMETHYLETHYL)-3-[3-(4-FLUOROPHENYL)PROPYL]-5-METHYL-2-PYRIDINE CARBOXAMIDE

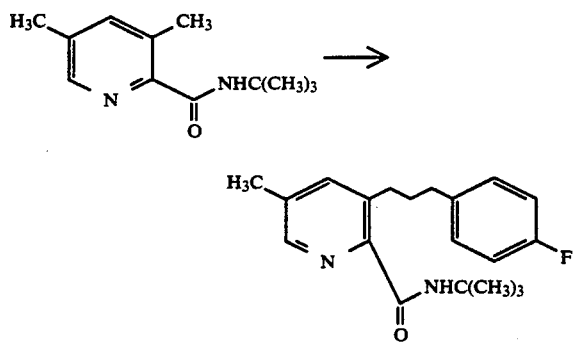

Cool a solution of N-(1,1-dimethylethyl)-3-methyl-2-pyridinecarboxamide in dry THF to −40° C. and add 2 equivalents of n-butyl lithium. Add a large excess of sodium bromide and stir for 15 minutes. Add 1 eq. of 4-fluorophenethyl chloride and stir for 2.5 hours while warming to −5° C. Quench the reaction with water and extract the product twice with ethyl acetate, then wash with brine (2X). Dry the organic phase over Na₂SO₄, filter and remove the solvent to produce the title compound.

F. 3-[3-(4-FLUOROPHENYL)PROPYL]-5-METHYL-2-PYRIDINE CARBONITRILE

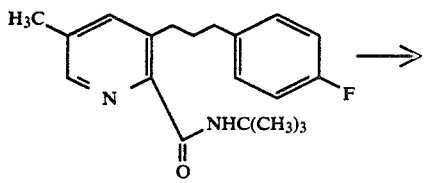

Heat the title compound of part E above in POCl₃ to 110° C. under an argon atmosphere for several hours. Pour the reaction mixture onto ice and basify with NaOH (50%) solution. Extract the mixture with ethyl acetate (3x) and wash with water. Wash with brine and dry over Na₂SO₄. Remove the solvent and pass the residue through a coarse SiO₂ (60–200 mesh) column to produce the title compound as a white solid.

G. 3-METHYL-10-FLUORO-5,6,7,12-TETRAHYDROBENZO[6,7]CYCLOOCTA[1,2-b]PYRIDIN-12-ONE

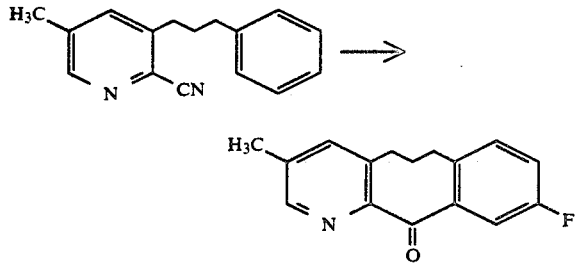

Cyclize the title compound of part F in polyphosphoric acid at 240° C. for several hours. Pour onto ice and basify with NaOH solution (50%). Extract the product with chloroform (3x) and wash with brine. Dry the organic phase with Na₂SO₄, filter and remove the solvent to produce the title compound.

H. 4-(3-Methyl-10-fluoro-5,6,7,12-tetrahydrobenzocycloocta[1,2-b]pyridin-12-ylidene)piperidine

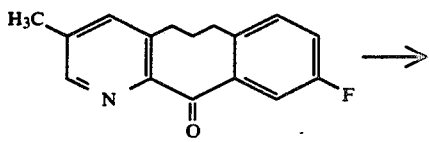

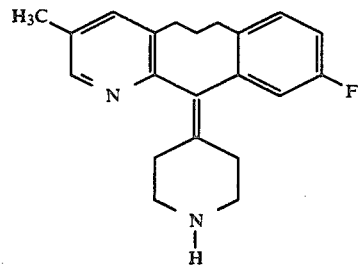

The carbonyl compound of part G above may be converted to the title compound as described in preparation example 3 above.

PREPARATIVE EXAMPLE 7

A. 2-Cyano-3-(bromomethyl)pyridine

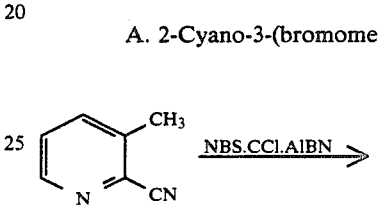

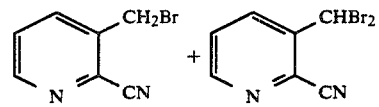

The title compound was prepared as described in Preparative Example 4, Part A.

B. 2-Cyano-3-(3-chlorophenylthiomethyl)pyridine

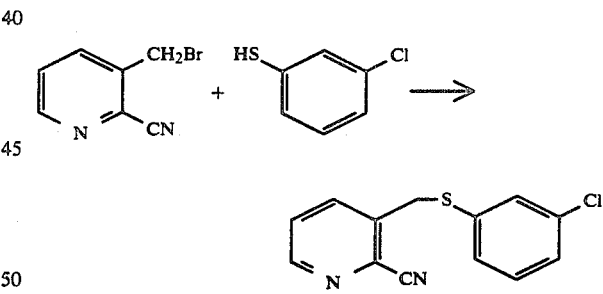

To a stirred, cloudy solution of sodium methoxide (14.7 g, 0.27 mol) in methanol (450 mL), contained in a water bath, add a solution of 3-chlorothiophenol (39.5 g, 0.27 mol) in methanol (95 mL). To the resultant solution add a solution of the title compound of Part A above (48.9 g, 0.25 mol) in methanol (195 mL), and stir the reaction mixture at room temperature for 1 h.

Concentrate the reaction mixture under reduced pressure, add 500 mL of ether to the residue, stir, and filter to remove sodium bromide. Evaporate ether under reduced pressure to obtain the title compound as an amber oil, which may be used without further purification in the following ring-closure process (Part C).

C.
8-Chloro-5,11-dihydro[1]benzothiepino[4,3-b]pyridin-11-one

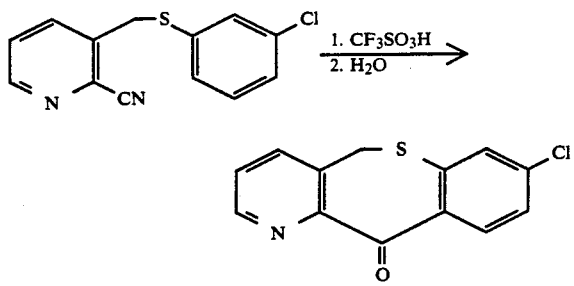

Stir a solution of the title compound from Part B above (49.7 g, 0.19 mol) in CF₃SO₃H (500 mL) for 3.5 h at 95° C. Allow the reaction mixture to cool below 60° C. and pour onto crushed ice (1500 mL). Stir the mixture for 0.5 h and add sufficient aqueous sodium hydroxide (220 mL of 50% solution) to raise the pH to 9.

Extract the aqueous solution with ethyl acetate (1x), saturate with sodium chloride, and extract again (2x) with ethyl acetate. Wash the combined extracts with brine (3x), filter, and dry over anhydrous MgSO₄.

Remove solvent under reduced pressure, and chromatograph the residual material on silica gel, eluting with ethyl acetate-hexanes (3:2), to obtain the title ketone as a tan solid, mp 186°–187° c.

D.
1-Methyl-4-(8-chloro-11-hydroxy-5,11-dihydro[1]benzothiepino[4,3-b]pyridinyl)piperidine

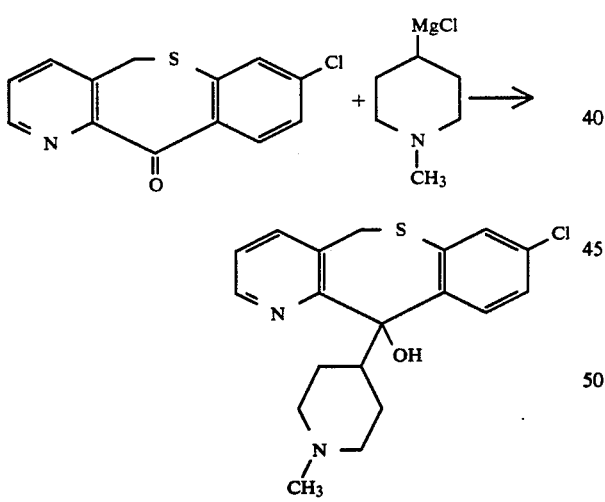

With cooling in an ice-water bath, add a suspension of the title ketone from Part C above (13.4 g, 51.2 mmol) in dry tetrahydrofuran (=THF; 52 mL) to a stirred solution (55 mL of approximately 1M) in THF of the Grignard reagent derived from 1-methyl-4-chloropiperidine. Stir the resultant mixture for 1 h at room temperature.

Quench the reaction by cooling the mixture to 10° C. in an ice-water bath and adding saturated aqueous ammonium chloride solution (50 mL). Add methylene chloride (100 mL), and stir the mixture for a few minutes. Filter the mixture through Celite, and wash the filter cake with methylene chloride. Combine the original filtrate and washes, separate the methylene chloride phase, and extract the aqueous phase (2x) with additional methylene chloride. Combine the extracts, wash with brine (2×75 mL), and dry over anhydrous sodium sulfate. Filter, strip the filtrate under reduced pressure, and chromatographed the residue on silica gel, eluting with methylene chloride-methanol-ammonium hydroxide (90:9:0.5), to obtain the title compound as an off-white to pale pink solid with mp 158.5°–159.5° C.

E.
1-Methyl-4-(8-chloro-5,11-dihydro-8 1]benzothiepino [4,3-b]pyridin-11-ylidene)piperidine

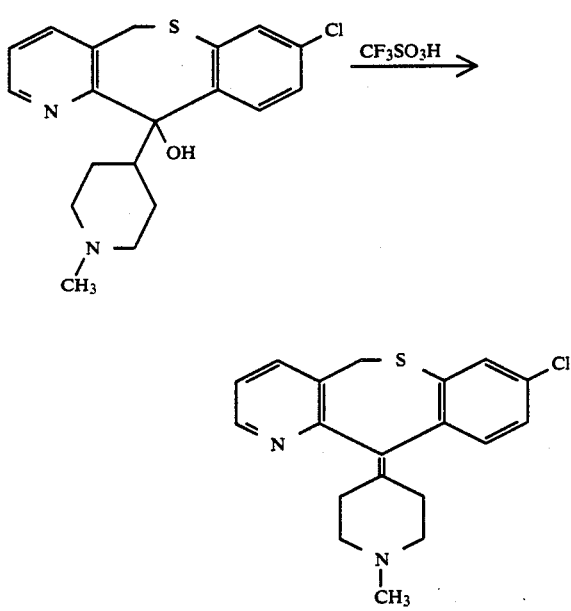

Heat a solution of the title compound from Part D above (5.04 g, 13.9 mmol) in CF₃SO₃H at 45° C. for 10.5 h. Cool the reaction solution to room temperature, and pour it into a stirred ice-water mixture. Maintain cooling in an ice-water bath, and add with stirring aqueous sodium hydroxide (130 mL of a 50% solution). Extract the solution with methylene chloride (3x), wash the combined extracts successively with water (2x) and brine (1x), dry over anhydrous sodium sulfate, and evaporate solvent under reduced pressure. Purify the residual glass by chromatographing on silica gel, eluting with methylene chloride-methanol-ammonium hydroxide (90:9:0.25), and triturating the solid thus isolated in acetonitrile. Filter to obtain the title compound as a light tan solid, containing 0.08 mole methylene chloride, mp 175°–177° C.

F.
1-Ethoxycarbonyl-4-(8-chloro-5,11-dihydro[1]benzo-thiepino[4,3-b]pyridin-11-ylidene)piperidine

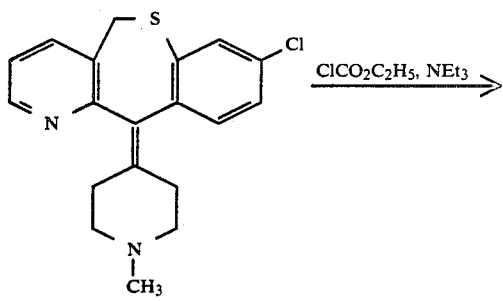

ClCO₂C₂H₅, NEt₃ →

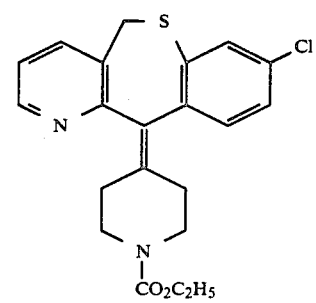

To a stirred solution of the title compound from Part E above (1.44 g, 4.2 mmol) and triethylamine (966 mg, 9.5 mmol) in dry toluene (27 mL), maintained at 80° C., add dropwise ethyl chloroformate (2.78 g, 25.6 mmol). After one hour, add more triethylamine (480 mg, 4.7 mmol), and continue heating at 80° C. for an additional hour.

Cool the reaction mixture to 50° C., add ethyl acetate (15 mL), wash successively with water (2x) and brine (1x), and dry over anhydrous magnesium sulfate. Filter, evaporate the filtrate under reduced pressure, and purify by chromatographing the residual solid on silica gel. Elute first with ethyl acetate-hexanes (9:1); then rechromatograph the partially purified material with ethyl acetate-hexanes (1:1) to obtain the title compound as an off-white solid with mp 154°–157° C.

G.
4-(8-Chloro-5,11-dihydro[1]benzothiepino[4,3-b]pyridin-11-ylidene)piperidine

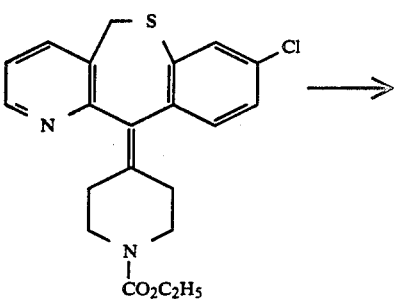

→

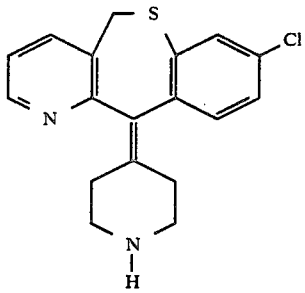

Reflux for 21.5 h in an inert gas atmosphere a solution of the title compound from Part F above (720 mg, 1.87 mmol) and potassium hydroxide (2.0 g, 35.6 mmol) in ethanol (20 mL)-water (2 mL).

Cool to room temperature, dilute with methylene chloride (20 mL), and wash successively with water (4x) and brine (1x). Dry the solution over anhydrous sodium sulfate, filter, and evaporate the filtrate under reduced pressure to obtain the title compound as an off-white solid, mp 206.5°–215° c.

EXAMPLE 1
1-Acetyl-4-(10H-[1]benzothiopyrano[3,2-b]pyridin-10-ylidene)piperidine

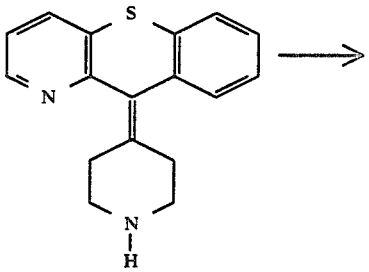

→

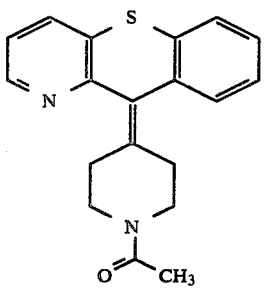

Dissolve the title compound from Preparative Example 1, part D (131 mg) in dry CH₂Cl₂ (6 ml) and add pyridine (57 )l) in CH₂Cl₂ (1 ml). Cool in an ice bath under an argon atmosphere and add dropwise CH₃C(O)Cl (50)L) in CH₂Cl₂ (2 ml). Stir the reaction while warming to room temperature over 30 minutes.

Dilute the reaction with CH₂Cl₂ and quench with dilute NaOH (0.5N, 50 ml). Separate off the organic layer and extract with CH₂Cl₂ (1X). Wash the organic layer with brine (1X), dry over Na₂SO₄, filter and remove the solvent. Azeotrope with toluene (1X) to yield a glassy solid (145 mg) which may be triturated with ethyl acetate and pentane.

Purify with flash chromatography, eluting with 5% CH₃OH in CH₂Cl₂ to yield the title compound as a white glassy solid (140 mg).

In the same manner 1-acetyl-2,6-dimethyl-4-(10H-[1]benzothiopyrano[3,2-b]pyridin-10-ylidene)piperidine was prepared from the title compound of preparative example 5, part B.

EXAMPLE 2

4-(10H-[1]benzopyrano[3,2-b]pyridin-10-ylidene)-1-piperidene carboxaldehyde

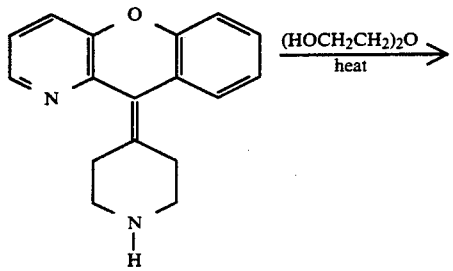

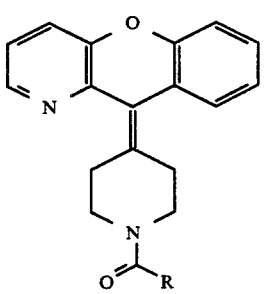

Reflux the title compound of Preparative Example 2, part C (13.1 g) in ethylformate (400 ml) on a steam bath for 12 hours.

Remove excess ethyl formate under vacuum to produce a brown oil.

Triturate the resultant brown oil with ethyl acetate to produce the title compound as a crystalline solid, which may be recrystallized from ethyl acetate. (7.5 g, m.p. 142°–145° C.).

EXAMPLE 3

1-Acetyl-4-(10H-[1]benzopyrano[3,2-b]pyridin-10-ylidene)piperidine

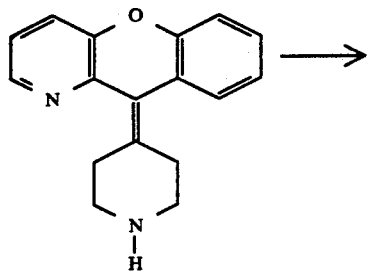

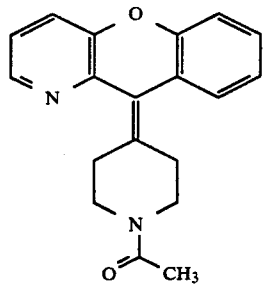

Dissolve the title compound of Preparative Example 2, Part C (304 mg) in dry CH₂Cl₂ (10 ml) and pyridine (0.456 ml).

Cool in an ice bath under an argon atmosphere and slowly add acetic anhydride (0.505 ml) in CH₂Cl₂ (2 ml). Stir the reaction while warming to room temperature over 30 minutes to yield the title compound in crude form.

Purify via flash chromatography eluting with 0%T3% CH₃OH in CHCl₃. Combine the appropriate fractions after removing the solvent, and triturate the solid with pentane (2X) to yield the title compound as a white solid (178 mg, m.p. 124°–126° C.).

EXAMPLE 4

1-Acetyl-4-(5,6,7,12-tetrahydrobenzo[6,7]cycloocta[1,2-b]pyridin-12-ylidene)piperidine

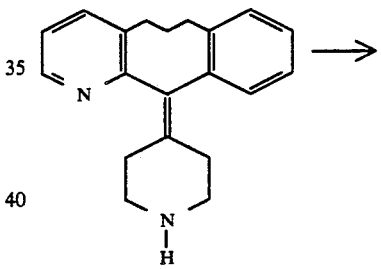

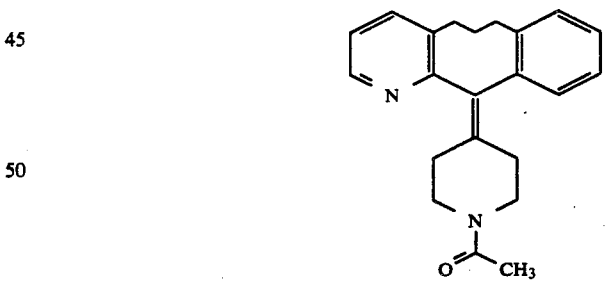

Dissolve the title compound of Preparative Example 3, Part H (302 mg, 1.04 mmol) in dry CH₂Cl₂ (10 ml) at 0° C. under an N₂ atmosphere. Add acetic anhydride (110 )l) dropwise.

After 4.5 hours, quench the reaction by pouring into aqueous NaOH (1N). Extract with CH₂Cl₂ (3X). Combine the organic portions, dry over MgSO₄, filter and rotary evaporate to dryness to produce the title compound as a glass (331 mg).

In the same manner 1-acetyl-4-(3-methyl-10-fluoro-5,6,7,12-tetrahydrobenzo[6,7]cycloocta[1,2-b]pyridin-12-ylidene)piperidine was prepared from the title compound of preparative example 6, part G.

EXAMPLE 5

1-Acetyl-4-(8-chloro-5,11-dihydro[1]benzoxepino[4,3-b]pyridin-11-ylidene)piperidine

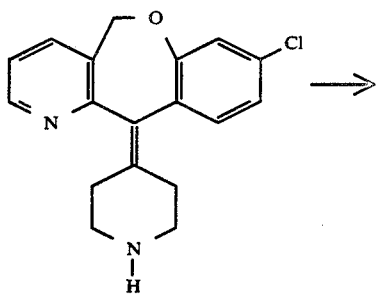

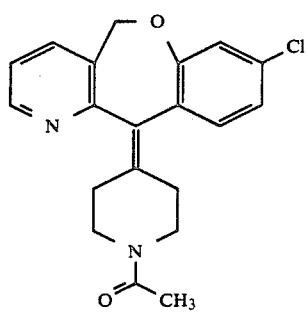

Dissolve the title compound from Preparative Example 4, part G (113 mg) in CH$_2$Cl$_2$ (4 ml). Add pyridine (58.4 )l) and cool the reaction. Add acetyl chloride (51.4 )l) and stir under an argon atmosphere for 1 hour.

Pour the reaction mixture in water and extract with CH$_2$Cl$_2$. Wash the combined organic portions with brine, and dry over Na$_2$SO$_4$.

Remove the solvent to produce the title compound as an off-white glass.

Purify the resultant compound with flash chromatography, eluting with 5% CH$_3$OH in CH$_2$Cl$_2$ to produce the title compound as a white glass (110 mg).

EXAMPLE 6

1-METHOXYACETYL-4-(5,6,7,12-TETRAHYDROBENZO[6,7]CYCLOOCTA[1,2-b]PYRIDIN-12-YLIDENE)PIPERIDINE

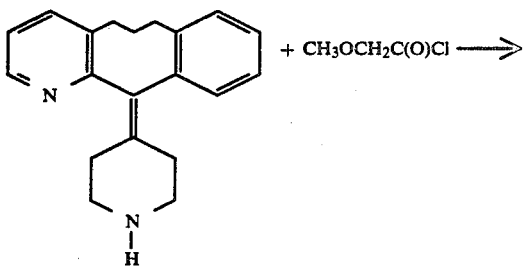

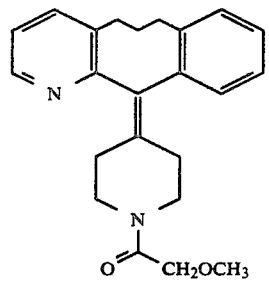

Dissolve the title compound of Preparative Example 3, part H, and pyridine in dry CH$_2$Cl$_2$ at 0° C. under an argon atmosphere. Add 1.1 equivalents of methoxyacetyl chloride dropwise, and slowly warm to room temperature. After 1.5 hours take up the mixture in CH$_2$Cl$_2$ and wash with brine. Dry over Na$_2$SO$_4$, filter, and concentrate in vacuo to obtain a residue, which may be purified via flash chromatography.

EXAMPLE 7

1-Acetyl-4-(8-chloro-5,11-dihydro[1]-benzothiepino[4,3-b]pyridin-11-ylidene)piperidine

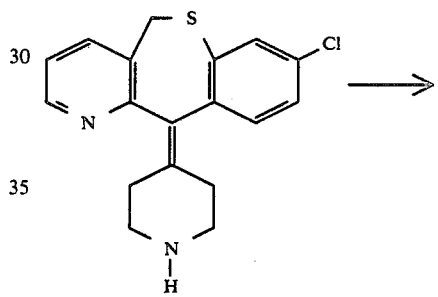

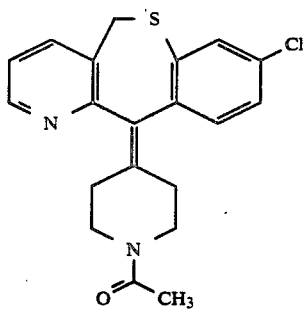

To a stirred solution of the title compound from Preparative Example 7, Part G, (470 mg, 1.43 mmol) and pyridine (225 mg, 2.84 mmol) in methylene chloride (21 mL), maintained at 10° C., add acetyl chloride (220 mg, 2.83 mmol) and stir the resultant solution at 10° C. for 45 minutes.

Add ice water (20 mL), and basify the mixture with 2.5M aqueous sodium hydroxide. Separate the layers, and extract the aqueous layer with methylene chloride (2x). Combine the extracts, wash with brine (1x), dry over anhydrous magnesium sulfate, filter, and evaporate the filtrate under reduced pressure. Chromatograph the residual glass on silica gel, eluting with methylene chloride-methanol-ammonium hydroxide (90:9:0.25); triturate the yellow powder thus obtained with hexanes; and filter to obtain the title compound as a very pale yellow hemihydrate, mp 80°–83.5° C. (dec).

EXAMPLE 8

1-Acetyl-4-(8-chloro-5,11-dihydro[1]-benzothiepino[4,3-b]pyridin-11-ylidene)piperidine-6-oxide

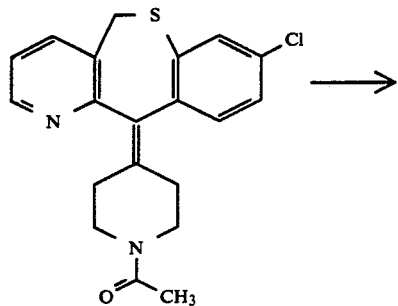

→

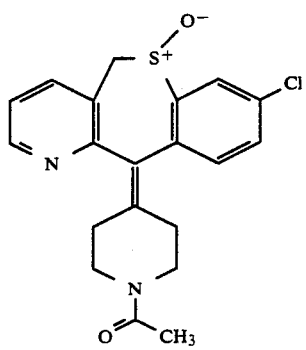

Add solid 3-chloroperoxybenzoic acid (59.4 mg of 80–85%, 0.293 mmol) to a stirred, cold (−50° C.) solution of the title compound from Example 7 above (109 mg, 0.293 mmol) in methylene chloride (7 mL), and stir the resultant solution at −50° C. for 1 h.

Wash the cold solution successively with 1.1M aqueous sodium bicarbonate (1x), water (2x), and brine (1x). Dry over anhydrous magnesium sulfate, filter, and evaporate solvent from the filtrate under reduced pressure. Triturate the residue with ether, and filter to obtain the ¼ hydrate of the title compound as a white solid, mp 209°–211° C. (dec).

EXAMPLE 9

(a) 1-Acetyl-4-(8-chloro-5,11-dihydro[1]-benzothiepino[4,3-b]pyridin-11-ylidene)piperidine-6,6-dioxide;

(b) 1-Acetyl-4-(8-chloro-5,11-dihydro[1]-benzothiepino[4,3-b]pyridin-11-ylidene)piperidine-1,6,6-trioxide;

(c) 1-Acetyl-4-(8-chloro-5,11-dihydro[1]-benzothiepino[4,3-b]pyridin-11-ylidene)piperidine-1,6-dioxide;

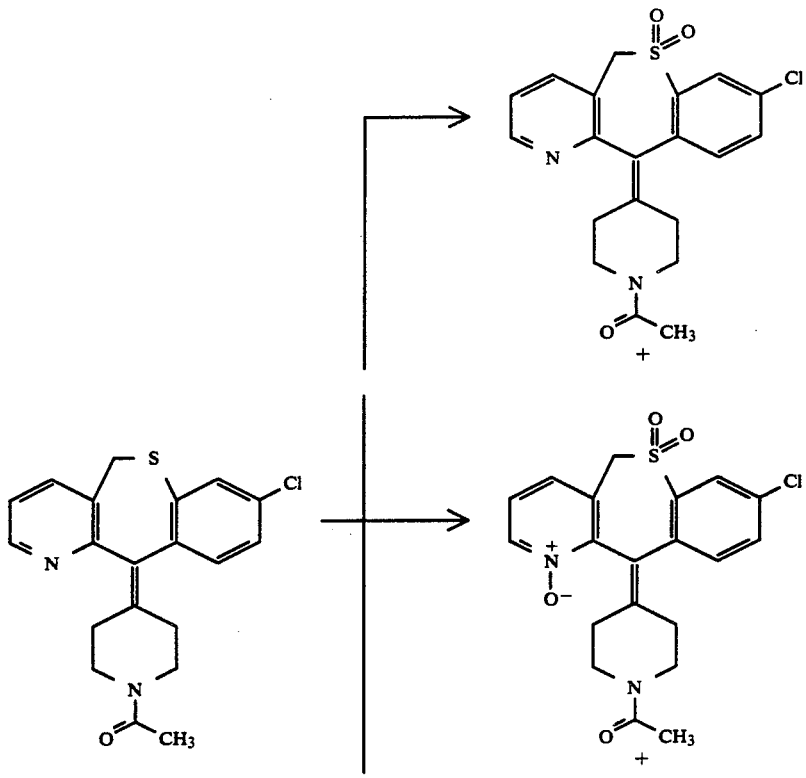

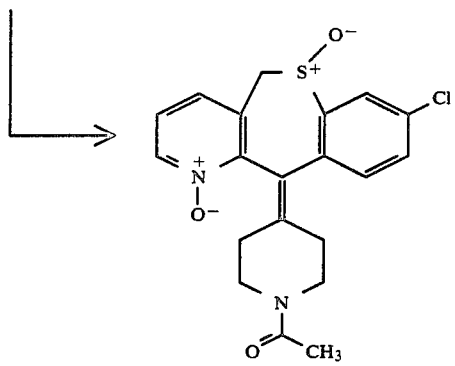

(a) Add solid 3-chloroperoxybenzoic acid (98.3 mg of 80-85%, K0.48 mmol) to a stirred, cold (−50° C.) solution of the title compound from Example 7 (202 mg, 0.546 mmol) in methylene chloride (6 mL). Stir for 1 h at −50° C., add a second quantity of 3-chloroperoxybenzoic acid (98.3 mg, K0.48 mmol), and stir for another hour at −50° C. Add a third portion of 3-chloroperoxybenzoic acid (9.4 mg, K0.046 mmol), and allow the reaction mixture to warm to room temperature. Stir at room temperature for 1 h, add a fourth quantity of the oxidant (9.4 mg, K0.046 mmol), and stir for a final 1 hour period.

Wash the reaction mixture successively with 1.1M aqueous sodium bicarbonate (1x) and brine (1x). Dry over anhydrous sodium sulfate, filter, and evaporate solent from the filtrate under reduced pressure. Chromatograph the residue on silica gel, eluting with methylene chloride-methanol-ammonium hydroxide (98:5:0.25) to obtain fractions corresponding to title compounds (a), (b), and (c), respectively. Rechromatograph on silica gel the fractions enriched in compound (a), eluting with methylene chloride-methanol-ammonium hydroxide (99:1:0.13) to obtain the title sulfone as a ¾ hydrate, mp 225°-228° C. (dec).

(b) Triturate in ether the solid derived from the chromatographic fractions containing compound (b), filter, and crystallize the solid from methanol-isopropyl ether. Triturate the crystalline product with ether, and filter to obtain the ¾ hydrate of the title sulfone N-oxide as a white solid, mp 238°-240° C. (dec).

(c) Triturate in ether the solid derived from the chromatographic fractions containing compound (c), and filter to obtain the title sulfoxide-N-oxide as a tan solid, mp 180°-184° C. (dec).

EXAMPLE 10

1-(4-Pyridinylcarbonyl)-4-(5,6,7,12-tetrahydrobenzocycloocta[1,2-b]pyridin-12-ylidene)piperidine N'-oxide

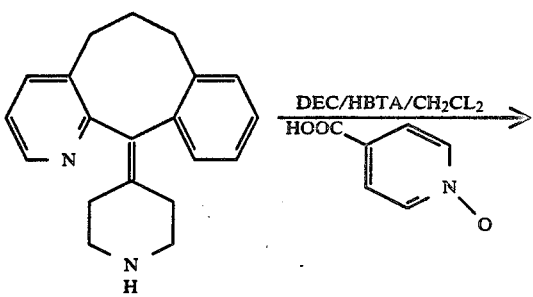

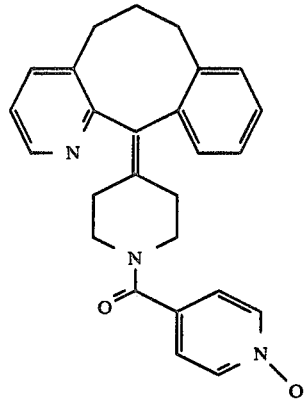

To a mixture of 4.50 g (15.5 mmol) of 4-(5,6,7,12-tetrahydrobenzocycloocta[1,2-b]pyridin-12-ylidene) piperidine, 2.19 g (15.7 mmol) of isonicotinic acid N-oxide, and 2.33 g (17.2 mmol) of 1-hydroxybenzotriazole hydrate in 30 mL of dry methylene chloride at −15° C. and under a nitrogen atmosphere was added dropwise over 25 min. a solution of 3.26 g (16.9 mmol) of 1-(3-dimethylaminopropyl)-3-ethylcarbodiimide hydrochloride in 60 mL of dry methylene chloride. The reaction mixture was slowly allowed to warm to room temperature. After 3 hours the mixture was poured into a solution of 10% aqueous sodium dihydrogen phosphate and extracted with methylene chloride (3x). The combined organic portions were dried over MgSO4, filtered, and concentrated in vacuo to give a product which was purified via flash chromatography to give 1-(4-pyridinyl carbonyl)-4-(5,6,7,12-tetrahydrobenzocycloocta[1,2-b]pyridin-12-ylidene)piperidine N-oxide as a colorless glass.

EXAMPLE 11

1-Acetyl-4-(9H-indeno[2,1-b]pyridin-9-yl)piperazine

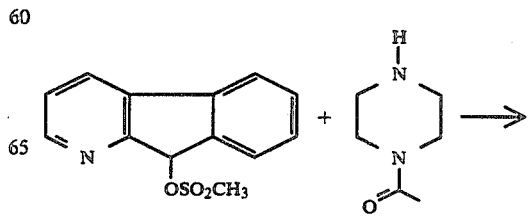

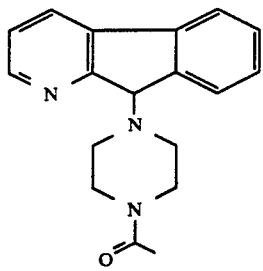

Intermediate compound XIV can be reduced with a reducing agent such as NaBH₄ to produce the corresponding alcohol. This can be converted to the corresponding 9-methyl sulfonyl indeno [2,1-b]pyridine.

A mixture of 68 mg (0.28 mmol) of 9-methylsulfonyl-9H indeno[2,1-b]pyridine, 76 mg of K$_2$CO$_3$ (0.55 mmol), and 59 mg (0.46 mmol) of N-acetyl piperazine in 10 ml of acetonitrile was heated at approximately 40° C. under a nitrogen atmosphere for 4 hours. The mixture was poured into water and extracted 3X with EtOAc. The organic layers were combined, washed with brine, dried over MgSO₄, filtered and concentrated in vacuo. The residue was purified via flash chromatography (2-3% MeOH/NH$_3$ in CH$_2$Cl$_2$) to give 52 mg (65%) of the title compound as an off white solid.

The following are examples of pharmaceutical dosage forms which contain a compound of the invention. As used therein, the term "active compound" is used to designate the compound 1-acetyl-4-(12H-benzo[b]cycloocta[3,2-b]pyridin-12-ylidene)piperidine. The scope of the invention in its pharmaceutical composition aspect is not to be limited by the examples provided, since any other compound of structural formula I can be substituted into the pharmaceutical composition examples.

Pharmaceutical Dosage Form Examples

|  |  | Example A Tablets |  |
|---|---|---|---|
| No. | Ingredient | mg/tablet | mg/tablet |
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix item nos. 1 and 2 in a suitable mixer for 10-15 minutes. Granulate the mixture with item no. 3. Mill the damp granules through a coarse screen (e.g., ¼") if needed. Dry the damp granules. Screen the dried granules if needed and mix with item no. 4 and mix for 10-15 minutes. Add item no. 5 and mix for 1-3 minutes. Compress the mixture to appropriate size and weight on a suitable tablet machine.

|  |  | Example B Capsules |  |
|---|---|---|---|
| No. | Ingredient | mg/capsule | mg/capsule |
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|  | Total | 250 | 700 |

Method of Manufacture

Mix item nos. 1, 2 and 3 in a suitable blender for 10-15 minutes. Add item no. 4 and mix for 1-3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

What is claimed is:

1. A compound represented by the structural formula

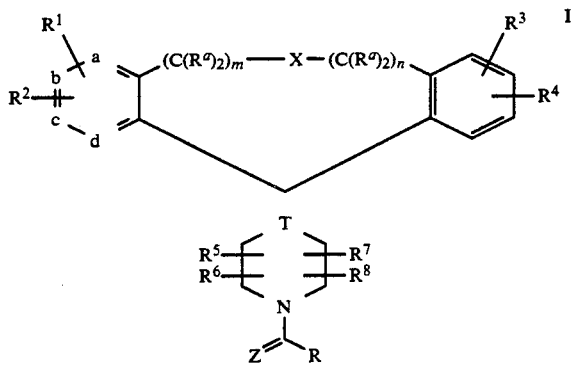

or a pharmaceutically acceptable salt or solvate thereof, wherein:

one of a, b, c and d represents nitrogen or —NR$^{11}$, where R$^{11}$ is —O$^-$, —CH$_3$, or —(CH$_2$)$_p$CO$_2$H where p is 1 to 3, and the remaining a, b, c and d groups are CH which may be optionally substituted with R$^1$ or R$^2$;

R$^1$ and R$^2$ may be the same or different and each independently represents halo, —CF$_3$, —OR$^{10}$, —C(O)R$^{10}$, —S(O)$_e$R$^{12}$ where e is 0, 1 or 2, —N(R$^{10}$)$_2$, —NO$_2$, SH, CN, —OC(O)R$^{10}$, —CO$_2$R$^{10}$, —OCO$_2$R$^{12}$, —NR$^{10}$C(O)R$^{10}$, C$_1$-C$_{20}$ alkyl, C$_2$-C$_{12}$ alkenyl or C$_2$-C$_{12}$ alkynyl, which alkyl or alkenyl groups may be substituted with halo, —OR$^{10}$ or —CO$_2$R$^{10}$, or R$^1$ and R$^2$ may together form a benzene ring fused to the pyridine ring;

R$^{10}$ represents H, C$_1$-C$_{20}$ alkyl or C$_6$-C$_{15}$ aryl;

R$^{12}$ represents C$_1$-C$_{20}$ alkyl or C$_6$-C$_{15}$ aryl;

R$^3$ and R$^4$ may be the same or different and each independently represents H or any of the substituents of R$^1$ and R$^2$, or R$^3$ and R$^4$ may be taken together to represent a saturated or unsaturated C$_5$-C$_7$ ring fused to the benzene ring;

R$^5$, R$^6$, R$^7$ and R$^8$ each independently represents H, —CF$_3$, —CO$_2$R$^{10}$, —C(O)R$^{10}$, C$_1$-C$_{20}$ alkyl or C$_6$-C$_{15}$ aryl, which alkyl or aryl may be substituted with —OR$^{10}$, —SR$^{10}$, —N(R$^{10}$)$_2$, —NO$_2$, —C(O)R$^{10}$, —OC(O)R$^{12}$, —OCO$_2$R$^{12}$, —CO$_2$R$^{10}$ and —OPO$_3$(R$^{10}$)$_2$, or one of R$^5$, R$^6$, R$^7$ and R$^8$ may be taken in combination with R as defined below to represent —(CH$_2$)$_r$—where r is 1 to 4, said combination being optionally substituted with C$_1$-C$_6$ alkyl, C$_1$-C$_6$ alkoxy, —CF$_3$ or C$_6$-C$_{15}$ aryl, or R$^5$ may be combined with R$^6$ to represent =O or =S, and/or R$^7$ may be combined with R$^8$ to represent =O or =S;

T represents carbon or nitrogen, with the dotted line attached to T representing an optional double bond when T is carbon;

m and n are integers 0, 1, 2, or 3, such that the sum of m plus n equals 0 to 3;

when m plus n equals 1, X represents —O—, —S(O)$_e$—wherein e is 0, 1 or 2, —NR$^{10}$—, —C(O)NR$^{10}$—, —NR$^{10}$C(O)—, —C(S)NR$^{10}$—, —NR$^{10}$C(S)—, —CO$_2$—or —O$_2$C—, where R$^{10}$ is a defined above;

when m plus n equals 2, X represents —O—, —S(O)$_e$—where e is 0, 1 or 2, or —NR$^{10}$;

when m plus n represents 0, X can be any substituent for m plus n equalling 1 and X can also be a direct bond, cyclopropylene or propenylene;

when m plus n equals 3 then X equals a direct bond; each R$^a$ may be the same of different, and each independently represents H, C$_1$-C$_6$ alkyl or phenyl;

Z represents =O, =S or =NR$^{13}$ with R$^{13}$ equal to R$^{10}$ or —CN, wherein R$^{10}$ is as defined above, such that (a) when Z is O, R may be taken in combination with R$^5$, R$^6$, R$^7$ or R$^8$ as defined above, or R represents H, C$_1$-C$_{20}$ alkyl, C$_6$-C$_{15}$ aryl, —SR$^{12}$, —N(R$^{10}$)$_2$, C$_3$-C$_{20}$ cycloalkyl, C$_2$-C$_{12}$ alkenyl, C$_2$-C$_{12}$ alkynyl or —D wherein —D represents C$_3$-c$_{15}$ heterocycloalkyl,

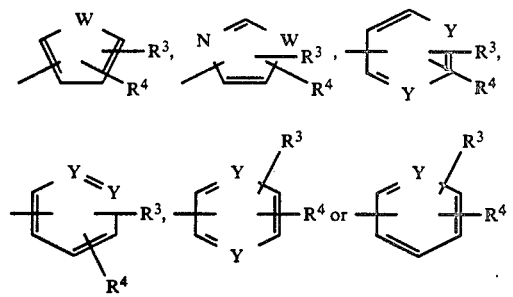

wherein R$^3$ and R$^4$ are as previously defined and W is O, S or NR$^{10}$, and where Y is N or NR$^{11}$, said cycloalkyl, alkyl, alkenyl and alkynyl being optionally substituted with from 1-3 groups selected from halo, —CON(R$^{10}$)$_2$, C$_6$-C$_{15}$ aryl, —CO$_2$R$^{10}$, —OR$^{14}$, —SR$^{14}$, —N(R$^{10}$)$_2$, —N(R$^{10}$)CO$_2$R$^{10}$, —COR$^{14}$, —NO$_2$ or —D, wherein —D and R$^{10}$ are as defined above and R$^{14}$ represents R$^{10}$, —(CH$_2$)$_r$OR$^{10}$ or —(CH$_2$)$_q$CO$_2$R$^{10}$ wherein r is 1 to 4, q is 0 to 4; said alkenyl and alkynyl R groups not containing —OH, —SH or —N(R$^{10}$)$_2$ on a carbon in a double or triple bond respectively; and (b) when Z represents =S, R represents in addition to those R groups above, C$_6$-C$_{15}$ aryloxy or C$_1$-C$_{20}$ alkoxy; and (c) where Z represents =NR$^{50}$, R represents H, C$_1$-C$_{20}$ alkyl, C$_6$-C$_{15}$ aryl, N(R$^{10}$)$_2$, C$_3$-C$_{20}$ cycloalkyl, C$_2$-C$_{12}$ alkenyl or C$_2$-C$_{12}$ alkynyl.

2. A compound as defined in claim 1 wherein d represents nitrogen or NO, and the a, b and c groups are CH which may be substituted with R$^1$ or R$^2$.

3. A compound as defined in claim 1 further characterized by one of R$^3$ and R$^4$ being halo, alkyl, —CF$_3$ or —OR$^{10}$.

4. A compound as defined in claim 3 further characterized by R$^5$, R$^6$, R$^7$ and R$^8$ being H or alkyl.

5. A compound as defined in claim 4 further characterized by m plus n equalling 1, and X representing —O—, —S(O)$_e$—, where e is 0, 1 or 2.

6. A compound as defined in claim 4 above further characterized by m plus n being zero, and X representing a direct bond, cyclopropylene, propenylene, —O—or —S(O)$_e$—with e equal to 0, 1 or 2.

7. A compound as defined in claim 4 above further characterized m plus n equalling 3 and X being a direct bond.

8. A compound as defined in claim 1 further characterized by T being carbon and the dotted line attached to T representing a double bond.

9. A compound as defined in claim 1 further characterized by T being nitrogen.

10. A compound as defined in claim 1 further characterized by Z being O and R representing H, alkyl, or D.

11. A compound as defined in claim 1 having the name:
1-acetyl-4-(10H-[1]benzothiopyrano[3,2-b]pyridin-10-ylidene)piperidine;
1-acetyl-4-(8-chloro-5,11-dihydro[1]benzoxepino[4,3]pyridin-11-ylidene)piperidine;
1-acetyl-4-(10H-[1]benzopyrano[3,2-b]pyridin-10-ylidene)piperidine;
4(10H-[1]benzopyrano[3,2-b]pyridin-10-ylidene)-1-piperidine carboxaldehyde;
1-acetyl-4-(5H-[1]benzopyrano[2,3-b]pyridin-5-ylidene)piperidine;
1-acetyl-4-(5,6,7,12-tetrahydrobenzo[6,7]cycloocta[1,2-b]pyridin-12-ylidene)piperidine;
1-methoxyacetyl-4-(5,6,7,12-tetrahydrobenzo[6,7]cycloocta[1,2-b]pyridin-12-ylidene)piperidine;
11-(1-acetyl-4-piperidinylidene)-8-chloro-5,11-dihydro-[1]-benzothiepino[4,3-b]pyridine;
11-(1-acetyl-4-piperidinylidene)-8-chloro-5,11-dihydro-[1]-benzothiepino[4,3-b]pyridine 1,6-dioxide;
11-(1-acetyl-4-piperidinylidene)-8-chloro-5,11-dihydro-[1]-benzothiepino[4,3-b]pyridine 6,6-dioxide;
11-(1-acetyl-4-piperidinylidene)-8-chloro-5,11-dihydro-[1]-benzothiepino[4,3-b]pyridine -6-oxide;
11-(1-acetyl-4-piperidinylidene)-8-chloro-5,11-dihydro-[1]-benzothiepino[4,3-b]pyridine -1,6,6-trioxide;
1-acetyl-4-(9H-indeno[2,1-b]pyridin-9-yl)piperazine; and
1-(4-pyridinylcarbonyl)-4-(5,6,7,12-tetrahydrobenzocycloocta[1,2b]pyridin-12-ylidene)piperidine N'-oxide.

12. A method of treating asthma, allergy and/or inflammation comprising administering to a mammal in need of such treatment an antiallergic effective amount of a compound as defined in claim 1.

13. A pharmaceutical composition comprising a compound of formula I as defined in claim 1 in combination with a pharmaceutically acceptable carrier wherein the active compound in a unit dose is about 0.01 mg to 2000 mg.